United States Patent
Havens et al.

(10) Patent No.: US 7,569,395 B2
(45) Date of Patent: Aug. 4, 2009

(54) METHOD AND APPARATUS FOR MEASURING OXYGEN CONCENTRATION

(75) Inventors: Marvin Russell Havens, Greer, SC (US); Darrell Carl Austin, Simpsonville, SC (US); Douglas James Paul, Seneca, SC (US)

(73) Assignee: Cryovac, Inc., Duncan, SC (US)

( * ) Notice: Subject to any disclaimer, the term of this patent is extended or adjusted under 35 U.S.C. 154(b) by 702 days.

(21) Appl. No.: 11/375,557

(22) Filed: Mar. 13, 2006

(65) Prior Publication Data

US 2007/0212792 A1     Sep. 13, 2007

(51) Int. Cl.
G01N 21/76 (2006.01)
G01N 21/64 (2006.01)
G01N 33/00 (2006.01)
G01N 7/00 (2006.01)

(52) U.S. Cl. .................. 436/172; 436/127; 436/164; 422/55; 422/82.05; 422/82.07; 422/82.08; 422/82.11; 422/83; 422/84; 422/85

(58) Field of Classification Search .................. None
See application file for complete search history.

(56) References Cited

U.S. PATENT DOCUMENTS

| | | | |
|---|---|---|---|
| 4,285,697 A | 8/1981 | Neary | |
| 4,526,752 A | 7/1985 | Perlman et al. | |
| 4,772,560 A | 9/1988 | Attar | |
| 4,810,655 A | 3/1989 | Khalil et al. | |
| 4,820,606 A | 4/1989 | Miyasaka et al. | |
| 4,857,472 A | 8/1989 | Wolfbeis | |
| 5,043,286 A | 8/1991 | Khalil et al. | |
| 5,047,350 A | 9/1991 | Switalski et al. | |
| 5,057,277 A | 10/1991 | Mauze et al. | |
| 5,096,813 A | 3/1992 | Krumhar et al. | |
| 5,108,932 A | 4/1992 | Wolfbeis | |

(Continued)

FOREIGN PATENT DOCUMENTS

DE     197 19 422 A1     11/1998

(Continued)

OTHER PUBLICATIONS

Lakowicz, *The Principles of Fluorescence Spectroscopy—Second Edition*, pp. 4-6, 10-11, and 237-265, 1999.

(Continued)

*Primary Examiner*—Jill Warden
*Assistant Examiner*—Neil Turk
(74) *Attorney, Agent, or Firm*—Alston & Bird LLP

(57) ABSTRACT

An apparatus and non-invasive method of measuring oxygen by exciting a luminescent compound disposed in a container and then measuring the intensity of the light emitted by the excited luminescent compound as it relaxes to the ground state. A plot of emission intensity as a function of time results in an exponential decay curve the area of which is inversely proportional to the oxygen concentration. The oxygen concentration can be determined over a wide temperature range by measuring the temperature of the container and the emission intensity and then applying the following equation:

$$[O_2] = (A_{Ta}(T)^2 + B_{Ta}(T) + C_{Ta})(\text{tau})^2 + (A_{Tb}(T)^2 + B_{Tb}(T) + C_{Tb})(\text{tau}) + (A_{Tc}(T)^2 + B_{Tc}(T) + C_{Tc})$$

T is the measured temperature;
tau is the area of the exponential decay curve; and
$A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are coefficients that are specific to the luminescent compound being examined.

17 Claims, 11 Drawing Sheets

U.S. PATENT DOCUMENTS

| | | | |
|---|---|---|---|
| 5,114,676 | A | 5/1992 | Leiner et al. |
| 5,242,835 | A | 9/1993 | Jensen |
| 5,316,949 | A | 5/1994 | Bull et al. |
| 5,403,746 | A | 4/1995 | Bentsen et al. |
| 5,409,666 | A | 4/1995 | Nagel et al. |
| 5,439,648 | A | 8/1995 | Balderson et al. |
| 5,458,896 | A | 10/1995 | Porter |
| 5,483,819 | A | 1/1996 | Barmore et al. |
| 5,495,850 | A | 3/1996 | Zuckerman |
| 5,515,864 | A | 5/1996 | Zuckerman |
| 5,583,047 | A | 12/1996 | Blinka et al. |
| 5,617,812 | A | 4/1997 | Balderson et al. |
| 5,863,460 | A | 1/1999 | Slovacek et al. |
| 5,958,782 | A | 9/1999 | Bentsen et al. |
| 6,009,339 | A | 12/1999 | Bentsen et al. |
| 6,015,715 | A | 1/2000 | Kirschner et al. |
| 6,190,612 | B1 | 2/2001 | Berger et al. |
| 6,297,508 | B1 | 10/2001 | Barmore et al. |
| 6,325,978 | B1 | 12/2001 | Labuda et al. |
| 6,664,111 | B2 | 12/2003 | Bentsen et al. |
| 6,914,677 | B2 | 7/2005 | Mader et al. |
| 2003/0008400 | A1 | 1/2003 | Putnam et al. |
| 2003/0143118 | A1 | 7/2003 | Draaijer |
| 2003/0190262 | A1 | 10/2003 | Blazewicz et al. |
| 2004/0086749 | A1 | 5/2004 | Kennedy et al. |
| 2004/0131806 | A1 | 7/2004 | Barmore et al. |
| 2004/0171094 | A1 | 9/2004 | Klimant et al. |
| 2004/0185154 | A1 | 9/2004 | Garwood |
| 2006/0171845 | A1 | 8/2006 | Martin et al. |

FOREIGN PATENT DOCUMENTS

| | | |
|---|---|---|
| EP | 0 252 578 A2 | 1/1988 |
| EP | 0 524 021 | 9/1997 |
| GB | 2 132 348 | 5/1987 |
| JP | 2003307513 | 10/2003 |
| WO | WO 87/00023 A1 | 1/1987 |
| WO | WO 01/63264 | 8/2001 |
| WO | WO 01/69243 A1 | 9/2001 |
| WO | WO 02/099416 | 12/2002 |
| WO | WO 2004/052644 | 6/2004 |
| WO | WO 2005/059500 A1 | 6/2005 |

OTHER PUBLICATIONS

Carraway et al., "Photophysics and Photochemistry of Oxygen Sensors Based on Luminescent Transition-Metal Complexes," *Analytical Chemistry*, vol. 63, No. 4, Feb. 15, 1991, pp. 337-342.

Draxler et al., "Effects of Polymer Matrices on the Time-Resolved Luminescence of a Ruthenium Complex Quenched by Oxygen," *J. Phys. Chem.*, vol. 99, No. 10, 1999, pp. 3162-3167.

Colvin, Jr., et al., "A Novel Solid-State Oxygen Sensor," *Johns Hopkins APL Technical Digest*, vol. 17, No. 4, 1996, pp. 377-385.

Debye, *Physikalische Zeitschrift*, XX, 1919, pp. 183-188.

Atkinson, "Monitoring—Non-Invasive Method for Determining Oxygen in Food Packaging," *Food, Cosmetics and Drug Packaging*, Jun. 2000, 2 pages.

Bacon et al., "Determination of Oxygen Concentrations by Luminescence Quenching of a Polymer-Immobilized Transition-Metal Complex," *Analytical Chemistry*, vol. 59, No. 23, Dec. 1, 1987, pp. 2780-2785.

$O_2$xySense™ 4000B—Portable Oxygen Analyzer (3 pages) available at www.oxysense.com/4000.htm; www.oxysense.com/4000_2.1htm; www.oxysense.com/4000_3.htm; and www.oxysense.com/4000_4.htm, Jul. 28, 2005.

OxySense—How it Works (6 pages) available at www.oxysense.com/how_it_works.htm; www.oxysense.com/how_it_works2.htm; www.oxysense.com/how_it_works3.htm; www.oxysense.com/how_it_works4.htm; www.oxysense.com/how_it_works5.htm; www.oxysense.com/how_it_works6.htm, Jul. 28, 2005.

$O_2$xyDot™—R&D and Development Sensor (3 pages) available at www.oxysense.com/oxydot.htm; www.oxysense.com/oxydot_2.htm; www.oxysense.com/oxydot_3.htm, Jul. 28, 2005.

Fresnel Lens (1 page) available at www.hyperphysics.phy-astr.gsu.edu/hbase/geoopt/fresnellens.html, Aug. 1, 2005.

Whatis.com—Solid State (2 pages) available at www.whatis.techtarget.com/definition/0,,sid9_gci500174,00.html, Aug. 2, 2005.

Hannemann, B. et al., *The Influence of Temperature of the Luminescence Decay Time on the Behaviour of a Luminescence Quenching Oxygen Sensor*, SPIE, vol. 2388, 1995, pp. 385-388.

Lam, S. K. et al., *Characterization of Phosphorescence Oxygen Sensor Based on Erythrosin B in Sol-Gel Silica in Wide Pressure and Temperature Ranges*, Sensors and Actuators B, Elsevier Sequoia S.A., vol. 73, No. 2-3, 2001, pp. 135-141.

Ogurtsov, V. I. et al., *Modelling of Phase-Fluorometric Oxygen Sensors: Consideration of Temperature Effects and Operational Requirements*, Sensors and Actuators B, Elsevier Sequoia S.A., vol. 113, No. 2, 2006, pp. 917-929.

Search Report for PCT/US2007/063804 dated Aug. 17, 2007.

Search Report for PCT/US2007/063809 dated Aug. 17, 2007.

METHOD AND APPARATUS FOR MEASURING OXYGEN CONCENTRATION

FIELD OF THE INVENTION

The invention relates generally to oxygen concentration measurements and more particularly to oxygen concentration measurements within packaging materials that are measured by using an oxygen sensitive luminescent compound.

BACKGROUND OF THE INVENTION

It is generally known that reducing the exposure to oxygen of oxygen sensitive articles maintains and enhances the quality and shelf life of the article. For instance, reducing the oxygen exposure of oxygen sensitive food products in a packaging system maintains the quality of the food product and avoids food spoilage. Foods, beverages, pharmaceuticals, medical devices, corrodible metals, analytical chemicals, electronic devices, and many other products may perish or experience diminished shelf life when stored too long in the presence of oxygen. Reduced oxygen exposure may help keep the product in inventory longer, thereby reducing costs incurred from waste and having to restock.

Manufacturers of packaging materials have developed packaging materials and systems to limit and/or control the amount of oxygen to which a packaged article may be exposed. Such materials and methods may include packaging articles in a package environment, or "headspace", with reduced oxygen levels. Modified Atmosphere Packaging (MAP) and vacuum packaging are two methods that are commonly used to control the amount of oxygen in a package. MAP involves the modification of the head space gas in a package in order to prolong the shelf life of the product it contains. In some MAP applications, the headspace may have substantially no oxygen. In other MAP applications, the headspace may have a predetermined level of oxygen. The success of MAP generally depends on the ability to control the concentration of oxygen within the package. In vacuum packaging, the atmosphere may be substantially removed so that the package environment is substantially free of oxygen.

In MAP applications for meat products, the raw meat may be packaged in a low level oxygen ($O_2$) environment. Packaging systems having low levels of oxygen are desirable because the fresh quality of meat can generally be preserved longer under anaerobic conditions than under aerobic conditions. Maintaining low levels of oxygen minimizes the growth and multiplication of aerobic bacteria. One example of a modified atmosphere environment is a mixture of gases consisting of about 30 percent carbon dioxide ($CO_2$) and about 70 percent nitrogen ($N_2$). Typically, low oxygen packaging environments may provide an atmosphere that helps prevent or inhibit excessive metmyoglobin (brown) formation in red meat products. In some MAP applications, it may be desirable to maintain the oxygen level at a predetermined concentration.

Another method of reducing oxygen exposure is to incorporate an oxygen scavenging composition into the packaging structure, such as in a film or tray. Oxygen scavenging compositions are compositions that consume, deplete, or reduce the amount of oxygen in a given environment. There are a wide variety of different compositions that can be used in oxygen scavenging applications. Exemplary compositions are described in U.S. Pat. Nos. 5,211,875; 5,350,622; 5,399,289; and 5,811,027 to Speer et al. and WO 99/48963 to Cai et al. The oxygen scavenging compositions can be "triggered" by exposing the composition to a radiation source, such as actinic radiation, having sufficient power for a sufficient amount of time to initiate oxygen scavenging.

Methods of triggering oxygen scavenging compositions typically use low-pressure mercury germicidal lamps that have an intensity output from about 5 to 10 mW/cm². These lamps are commonly referred to as germicidal since the principal emission is at 254 nm. A dosage of UV-C light between about 100 to 1600 mJ/cm² is typically needed to trigger oxygen scavenging. For details on preferred methods for activating such oxygen scavenging compositions at point of use, see Speer et al., U.S. Pat. No. 5,211,875, Becraft et al., U.S. Pat. Nos. 5,911,910, and 5,904,960, and co-pending applications U.S. Ser. No. 09/230,594 filed Aug. 1, 1997, and Ser. No. 09/230,776 filed Jul. 29, 1997, and U.S. Pat. No. 6,233,907 (Cook et al.), all of which are incorporated herein by reference in their entirety.

Unfortunately, oxygen scavengers do not always activate on command. This may result from a number of factors, including defective scavenger compositions, inadequate triggering conditions, operator error, or a combination of these or other factors. In many instances, it may not be readily apparent whether the oxygen scavenging composition is defective or whether the failure originated in the triggering equipment. Typically, conventional oxygen scavengers do not themselves visually indicate whether or not they are active. In response to this uncertainty, operators of packaging assembly plants prefer to verify scavenger activity as soon as possible after triggering. The longer a failed triggering attempt remains undiscovered, the more waste and expense is incurred, especially where packaging equipment operates at high speeds.

In addition, defective seals or openings in the packaging may permit oxygen to enter into the headspace within a package. Such defective packages may not be easily discernable. As a result, a packaged article may be exposed to an undesirable level of oxygen, which may result in loss of shelf-life or spoilage.

There are several methods for verifying oxygen concentration in a package. Prior art methods for verifying oxygen scavenger activity in a low oxygen package involve detecting oxygen concentrations in the package headspace. Oxygen concentrations are typically measured after the package has been assembled and equilibrium of oxygen levels established among the headspace, package layers, and package contents. Detection of sufficiently reduced oxygen levels within the headspace allows one to determine if the package has maintained a low oxygen atmosphere and to infer whether an oxygen scavenging compound has been successfully activated.

Under this approach, one typically has two options, neither of which is particularly satisfactory. One option is to leave an oxygen indicator in the package headspace after it has been assembled and sealed. For example, Mitsubishi teaches an indicator comprising glucose and methylene blue, encased within a sachet. The sachet is left inside the package after it is sealed. A color change within the sachet indicates the presence of unwanted oxygen.

This approach has several disadvantages, however. Sachets must be attached to the package to avoid their being accidentally ingested by the consumer. Some package contents require a moisture-free storage environment. Yet, in the case of the Mitsubishi glucose/methylene blue indicator, moisture may be required to produce a color change. Also, sachets potentially introduce contaminants or other substances into the package that may be incompatible with its contents or accidentally ingested. For some applications, manufacturers may not want to leave indicators in packages where consumers may misinterpret the information the indicator provides.

Another option is to use probes to measure the gas content within the headspace. One commonly used headspace gas analyzer is available from Mocon, Inc. Unfortunately, the use of probes that rely on gas chromatography and other such analytical techniques typically requires removing a sample of the atmosphere within the package. This technique invariably requires some sort of device that will penetrate the package and remove a portion of the gas within the headspace. The device inevitably leaves a hole in the package, destroying the integrity of the package. As a result, this may require sacrificing the sampled package.

Additional methods of measuring oxygen concentration include the use of luminescent compounds that may be incorporated into the film lidding or into an interior space of the package itself. When exposed to light at a proper wavelength, the molecules of the luminescent compound can absorb energy which may cause electrons to move from a ground state energy level into an excited state energy level. From here, the excited molecules relax back to the ground state through a process known as vibrational relaxation. In vibrational relaxation, the absorbed energy is transferred to surrounding molecules through molecular collisions.

Alternatively, the molecule may relax to the ground state by emitting a photon. In some molecules, the electron may move from a high energy singlet state into a high energy triplet state before emitting a photon and returning to the ground state. A transition from the high energy singlet state is called fluorescence. Fluorescence transitions have a relatively short life, on the order of $10^{-8}$ to $10^{-4}$ seconds. Transitions from the triplet state to the ground state are called phosphorescence. Phosphorescence transitions are relatively longer than fluorescence transitions and may be on the order of $10^{-4}$ to $10^{-2}$ seconds.

Both fluorescence and phosphorescence transitions are quenched by oxygen. In 1919, Stern and Volmer reported that oxygen quenches the luminescence of certain compounds. From their experiments, they determined that the quenching-related decrease in luminescent intensity or lifetime of the excited state may be correlated to the oxygen concentration. This correlation may be expressed by the Stern-Volmer equation:

$$\frac{F_0}{F} = \frac{\tau_0}{\tau} = 1 + k_q \tau_0 [Q] \tag{1}$$

Wherein:

$F_0$ is the intensity of the luminescence in absence of oxygen;

F is the intensity of the luminescence in presence of oxygen;

$\tau_0$ is the lifetime of the excited state in the absence of oxygen;

$\tau$ is the lifetime of the excited state in the presence of oxygen;

$k_q$ is the bimolecular quenching constant; and

[Q] is the concentration of oxygen.

A plot of $F_0/F$ or $\tau_0/\tau$ versus [Q], also known as a Stern-Volmer plot, is expected to provide a linear plot because $F_0/F$ and $\tau_0/\tau$ are generally linearly dependent on the oxygen concentration. A plot of the Stern-Volmer equation includes a y-intercept of 1 and a slope of $k_q\tau_0$, which is also referred to as the Stern-Volmer constant K. From the Stern-Volmer plot, the concentration of oxygen may be deduced by measuring the intensity of the luminescence or the lifetime of the excited state ($\tau$). This relationship has been used in the prior art to determine the oxygen concentration. However, both the intensity of the luminescence and the lifetime of the excited state are a function of temperature as well as oxygen concentration. Both luminescence intensity and the lifetime of the excited state will change at varying temperatures. As a result, prior art devices utilizing the Stern-Volmer equation to determine oxygen concentration have been limited to isothermal conditions. Measuring the intensity or lifetime at temperature conditions that are different from the initial Stern-Volmer plot may produce results that are inaccurate and do not reflect the actual oxygen concentration. Accordingly, there still exists a need for a non-invasive method and device that may be used to accurately measure oxygen concentrations under various temperature conditions.

BRIEF SUMMARY OF THE INVENTION

The invention provides an apparatus and method of accurately measuring oxygen concentration that overcomes many of the aforementioned problems. In one embodiment, the invention includes a method of determining the oxygen concentration within a sealed container. The method includes exciting a luminescent compound and then measuring the intensity of the light emitted by the excited luminescent compound as it relaxes to the ground state. The intensity of the emitted light is inversely proportional to the oxygen concentration. In one embodiment, the emission of excited light as a function of time produces an exponential decay curve, with a characteristic tau value. Applicants have discovered that the oxygen concentration can be determined over a wide temperature range by applying the following equation:

$$[O_2] = (A_{Ta}(T)^2 + B_{Ta}(T) + C_{Ta})(\text{tau})^2 + (A_{Tb}(T)^2 + B_{Tb}(T) + C_{Tb})(\text{tau}) + (A_{Tc}(T)^2 + B_{Tc}(T) + C_{Tc}) \tag{6}$$

Wherein:

T is the measured temperature;

tau is the coefficient of the exponential decay curve; and $A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are previously determined coefficients that are specific to the luminescent compound being examined and that describe the intensity of the luminescent compound as a function of oxygen concentration and temperature. As a result, the measurement of oxygen concentration is not limited to isothermal conditions.

The method and apparatus use a luminescent compound that is disposed in the interior of the container. Exciting the luminescent compound results in a luminescent emission that may be measured externally from the container's interior. As a result, the oxygen concentration may be measured within a container without having to penetrate or physically damage the container. In one embodiment, the luminescent compound comprises a metal porphyrin that undergoes a phosphorescent transition.

In one embodiment, tau may be determined by measuring the emission intensity of the luminescent compound as it relaxes to the ground state. A plot of intensity as a function of time results in an exponential decay curve, from which tau can be determined. In one embodiment, tau is determined by irradiating the luminescent compound with light having a wavelength that is strongly absorbed by the luminescent compound so that the luminescent compound is promoted into an excited state. The irradiation of the luminescent compound is terminated when the luminescent compound achieves a steady state between excitation and luminescence. In a next step, luminescent intensity of the excited luminescent compound is measured over a period of time to produce an exponential decay curve, from which tau can be determined.

In one embodiment, tau can be calculated from the area of the decay curve. In some embodiments, the area of exponential decay curve is calculated by measuring luminescent intensity over a period of time in which intensity measurements are taken every 1 to 100 microseconds to create a plurality of discrete time segments. The irradiation and measurement steps may then be repeated n number of times, wherein n is from about 10 to 2500 to create n number of discrete time segments. The time segments may then be summed to create an average signal for n number of times. Averaging the signal helps to reduce the level of noise and thereby increase the sensitivity of the method and apparatus.

In another embodiment, calculating the area of the exponential decay curve includes determining a baseline for the exponential decay curve at a value of 4 tau or greater, subtracting the baseline from all summed time segments, normalizing the summed time segments, and then integrating the summed time segments to determine tau. In some embodiments, the baseline may be determined at a value greater than 8 or 10 tau.

In yet another embodiment, the invention includes an apparatus for measuring oxygen concentration. In one embodiment, the apparatus may include an excitation source that is configured to generate excitation light having a wavelength that causes a luminescent compound to be promoted into an excited energy state. A detector disposed in a position to receive luminescent light emitted by the excited luminescent compound converts the luminescent light into an electronic signal. A control unit in communication with the detector then uses one or more algorithms to calculate the oxygen concentration within the container being examined. The use of a luminescent compound permits the analysis of the composition without having to penetrate or damage the container.

In one embodiment, the apparatus may also include focusing optics disposed between the detector and the luminescent compound. The focusing optics may be configured to collect and intensify the luminescent light against the detector so that the signal of the luminescent light may be magnified without the use of electronic amplifiers. As a result, the apparatus may have increased sensitivity independent of electronic amplifiers.

Temperature also affects the luminescent intensity and the value of tau because oxygen quenching is a diffusion controlled process. At higher temperatures, the diffusion rate of oxygen increases which results in a greater amount of collisional quenching, and hence lower intensities and smaller tau values. Conversely, at lower temperatures the diffusion rate of oxygen is decreased which results in relatively higher emission intensities and greater tau values. The temperatures at which oxygen sensitive products are maintained may vary widely from product to product. Accordingly, it is important to account for temperature when using luminescent compounds to measure the oxygen concentration within a container. Applicants have discovered that the oxygen concentration can be determined over a wide temperature range by applying the following equation:

$$[O_2]=(A_{Ta}(T)^2+B_{Ta}(T)+C_{Ta})(\text{tau})^2+(A_{Tb}(T)^2+B_{Tb}(T)+C_{Tb})(\text{tau})+(A_{Tc}(T)^2+B_{Tc}(T)+C_{Tc})$$

wherein:

T is the measured temperature;

tau is the area of the exponential decay curve; and $A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are previously determined coefficients that are specific to the luminescent compound being examined and that describe the intensity of the luminescent compound as a function of oxygen concentration and temperature. In one embodiment, the apparatus includes a control unit that is in communication with the detector and that is configured to calculate the oxygen concentration within the container using the above equation.

The Applicants have also discovered that limiting heat from the surrounding environment and from the electronics of the apparatus may help improve the accuracy of the calculated oxygen concentration. To help improve the accuracy of the temperature measurement the apparatus may include an insulating member that is disposed between the apparatus housing and an outer surface of the container. The insulating member helps thermally isolate the container from the housing. One or more temperature sensors may be disposed adjacent to the insulating member so that the temperature sensors are also thermally isolated from the housing. The insulating member may also help thermally isolate the temperature sensors from the surrounding environment. The insulating member can comprise any suitable material that can be used to thermally isolate the temperature sensors. Suitable materials may include thermoplastic or thermoset polymeric materials.

In another embodiment, the apparatus may comprise a handheld device that may permit a user to relatively easily manipulate and position the apparatus in a oxygen measuring relationship with a container that is being examined. In one embodiment, the handheld device may have a "gun-like" shape. The apparatus may also include a user interface panel having a visual display and a user interface which may permit an operator to scroll through and select various menu options.

In one embodiment, the apparatus may include a control unit that can be internal or external to the apparatus. The control unit is configured to control the operation of the apparatus and its various components. The control unit can also include a memory component, such as storage device, from which the control unit recalls one or more algorithms, operational parameters, and the 9 previously determined coefficients that are used in connection with equation (6) above. The control unit may also include one or more algorithms that are encoded therein. In one embodiment, operational parameters and the luminescent specific coefficients are stored in the memory component from which the luminescent specific coefficients and operational parameters for a specific luminescent compound are recalled. As a result, the apparatus provides a dynamic instrument that can be optimized for use with a wide variety of luminescent compounds.

Thus, the invention provides a method and apparatus that overcomes many of the problems associated with measuring oxygen concentration in a sealed container and that can be used to measure oxygen concentration over a wide temperature range.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

The invention is directed to a non-invasive apparatus and method for measuring oxygen concentration within a sealed container, such as a sealed package. In one embodiment, the apparatus and method include exciting a luminescent compound that is disposed in the sealed container and then measuring the resulting luminescent intensity as a function of time. The luminescent intensity data may then be used to calculate the concentration of oxygen in the sealed container. The apparatus and method utilize a series of unique operational steps and algorithms to obtain and analyze the intensity data. In one embodiment, the apparatus and method include a temperature sensor that may be used to determine the temperature of the luminescent compound. The measured temperature may be used in combination with one or more algorithms to determine the oxygen concentration over a broad temperature range without having to penetrate or remove a gas sample from within the sealed container.

In the context of the invention, the term "container" includes, but is not limited to, a package including case-ready packages, pouches, bags, boxes, carton, envelopes, bottles, and like. The term "container" also includes any packaging that has been designed to maintain a high or low oxygen atmosphere and includes a surface through which light of interest can be transmitted.

In one embodiment, a luminescent compound is positioned in an interior space of the container. The luminescent compound may be positioned within the container in an orientation that permits collisions between the luminescent compound and any oxygen molecules that are present within the container. To measure the oxygen concentration, the apparatus, which is capable of exciting the luminescent compound and measuring the emissions of the luminescent compound, is placed in an oxygen-measuring relationship with the luminescent compound. The apparatus may then emit light, referred to as "excitation light", that is capable of exciting the luminescent compound. A detector within the apparatus measures luminescent intensity of the excited compound as a function of time. From the measured intensity data, the apparatus performs a series of mathematical operations using one or more algorithms to determine the concentration of oxygen within the container.

Figure 1:
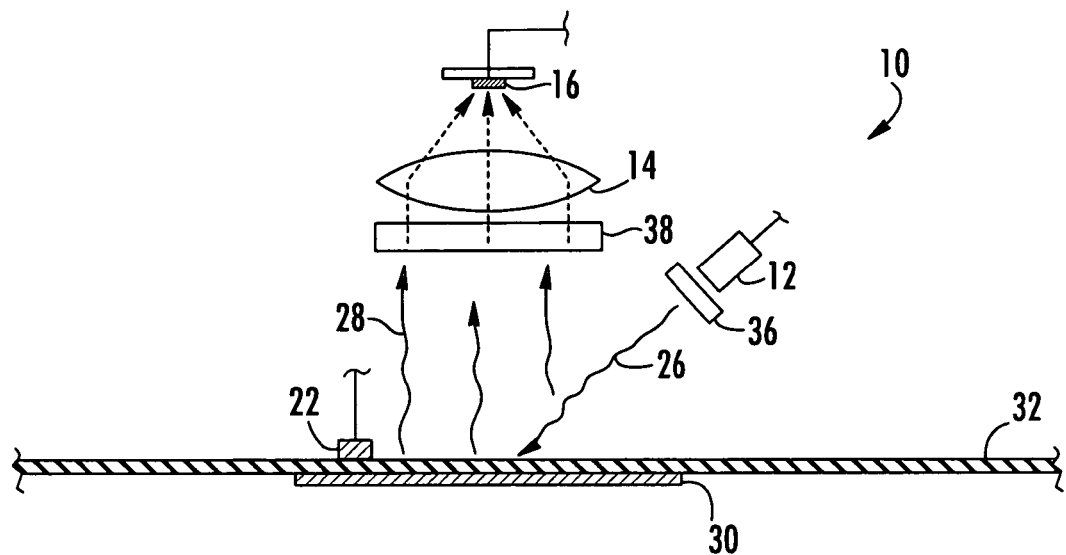
FIG. 1 is a schematic illustration of an apparatus for exciting a luminescent compound and measuring the resulting luminescent intensity to determine the oxygen concentration within a sealed container.

FIG. 1 is a schematic illustration of an apparatus 10 that is capable of determining the concentration of oxygen in a container. As shown, the apparatus is positioned in an oxygen-measuring relationship with a luminescent compound 30. In the context of the invention, an "oxygen-measuring relationship" refers to a position of the apparatus with respect to the container wherein excitation light from the apparatus is capable of reaching and exciting the luminescent compound and where luminescent light emitted by the compound is able to be detected by a detector. In some embodiments, the luminescent compound may be disposed adjacent to a surface of the container that is substantially transparent to the desired excitation light and the light emitted by the excited luminescent compound. In the illustrated embodiment, the enclosed container includes a window 32 that permits the transmission of excitation light and emission light. In one embodiment, the window 32 may comprise a substantially transparent material that permits the transmission of the excitation light and the light emitted by the excited luminescent compound, such as a film, laminate, web, sheet, or similar structure. The use of a luminescent compound within the container permits determination of the oxygen concentration of the headspace of the container without a need to physically sample the headspace within the container. As a result, the invention may be used to determine the oxygen concentration in a sealed container without having to penetrate or damage the sealed container.

In one embodiment, the apparatus 10 comprises an excitation source 12, focusing optics 14, and a detector 16. In operation, the excitation light source 12 emits light 26 having a wavelength that excites the luminescent compound 30. As the excited luminescent compound relaxes to the ground state it emits light 28 that is detectable by detector 16. Light emitted by the luminescent compound is referred to as "luminescent light." In the presence of oxygen, the intensity of such an emission is reduced based on the oxygen concentration in the container. The detector 16 produces an electric signal in response to luminescent light impacting the detector. The electronic signal may then be communicated to a control unit (not shown), such as a processor, that is configured to analyze the intensity data and calculate the oxygen concentration within the container. The apparatus may also include filters 36, 38 that filter out certain undesirable wavelengths of light.

The apparatus may also comprise a temperature sensor 22 that is capable of measuring the temperature of the outer surface of the window, and hence the temperature of the luminescent compound. The resulting temperature data is communicated to a control unit that uses the intensity data, measured temperature, and one or more algorithms to determine the oxygen concentration. The temperature sensor may be capable of accurately measuring the temperature of the container being evaluated within about ±0.1° C. The apparatus and method use a series of mathematical operations that permit the oxygen concentration within a container to be determined over a broad range of temperatures. As a result, the invention can be used to measure oxygen concentrations at various temperatures and is not limited to isothermal conditions.

As discussed above, Stern and Volmer reported that oxygen quenches the luminescence of certain compounds. In the absence of oxygen, the luminescence of the excited luminescent compound gradually decays as the excited compound returns to the ground state. In the presence of oxygen, the luminescence is quenched resulting in a relatively shorter decay rate. Generally, in both cases the decay rate follows an exponential decay curve wherein the exponential coefficient is known as $\tau$ (tau). The value of tau is related to the decay curve, which in turn is related to the oxygen concentration. High values of tau have slow decay rates and correspond to a low oxygen concentration, whereas low values of tau have a relatively faster decay rate and correspond to high oxygen concentrations. The value of tau is a property of the oxygen concentration and is independent of the amount of luminescent compound.

Figure 2:
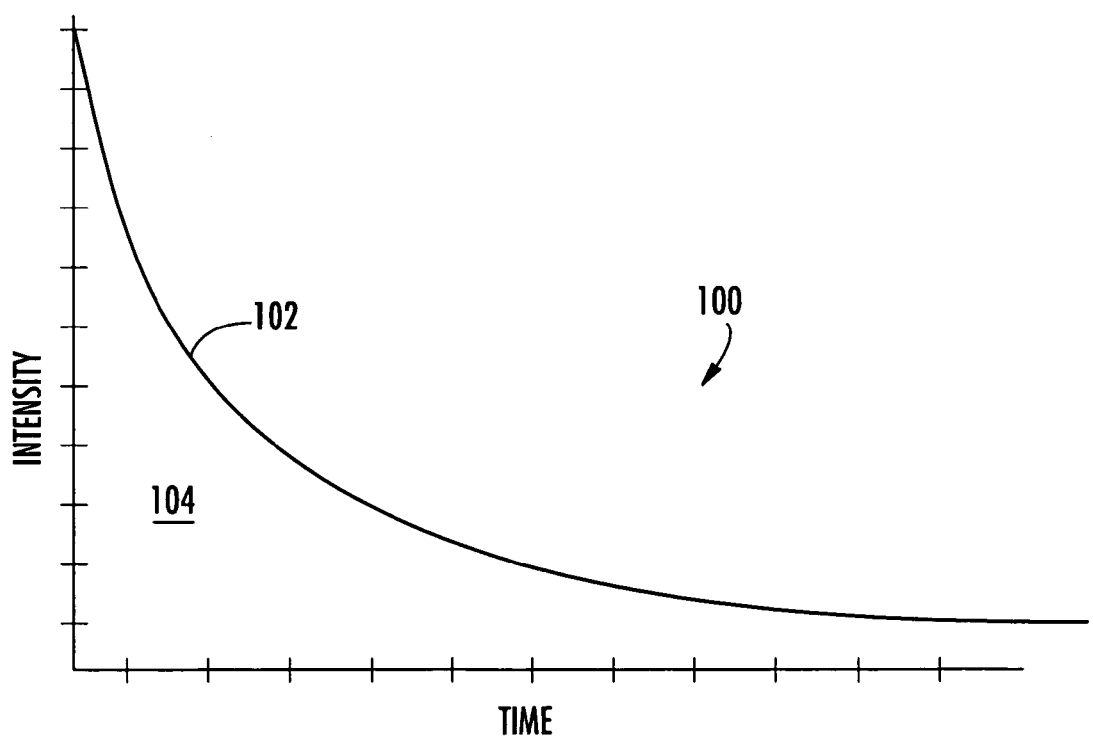
FIG. 2 is a representative illustration of an exponential decay curve for the emission of an luminescent compound as a function of time.

FIG. 2 is a graphical plot 100 illustrating a luminescent decay curve. Decay curve is a representation of the oxygen concentration in which luminescent intensity has been plotted as a function of time. As can be seen in FIG. 2, the graphical plot follows an exponential decay curve. From equation (1) above and FIG. 2, it can be seen that both intensity and tau are roughly proportional to $1/[O_2]$. As discussed in greater detail below, tau may be determined by exciting a luminescent compound and measuring the intensity as a function of time. From this intensity and time data, an exponential decay curve 102 may be determined, from which tau may be determined by calculating the area 104 under the curve.

As discussed above, temperature also affects the luminescent intensity and the value of tau. Oxygen quenching is a diffusion controlled process which results primarily from collisions between an oxygen molecule and an excited luminescent compound, also referred to as a fluorophore. In the context of the invention, the term "fluorophore" refers generally to luminescent compounds that are in an excited state and are capable of relaxing to the ground state by emitting a photon. Fluorophores include luminescent compounds that undergo fluorescence and/or phosphorescence transitions and that are capable of being quenched by oxygen. In collisional quenching, the quencher must diffuse to the fluorophore during the lifetime of the excited state. Generally, collisional quenching occurs without any permanent alteration or consumption of the colliding molecules. At higher temperatures, the diffusion rate of oxygen also increases which results in a greater amount of collisional quenching, and hence lower intensities and smaller tau values. Conversely, at lower temperatures the diffusion rate of oxygen is decreased which results in relatively higher emission intensities and greater tau values.

Stern-Volmer plots are typically not useful for determining oxygen concentrations over a range of temperatures because any individual plot must be determined under iso-thermal conditions. To attempt to create a Stern-Volmer plot at different temperatures would result in a non-linear plot. As discussed above, both intensity and tau are temperature dependent and therefore cannot be used reliably to determine oxygen concentration at different temperature conditions within the same plot.

Figure 3:
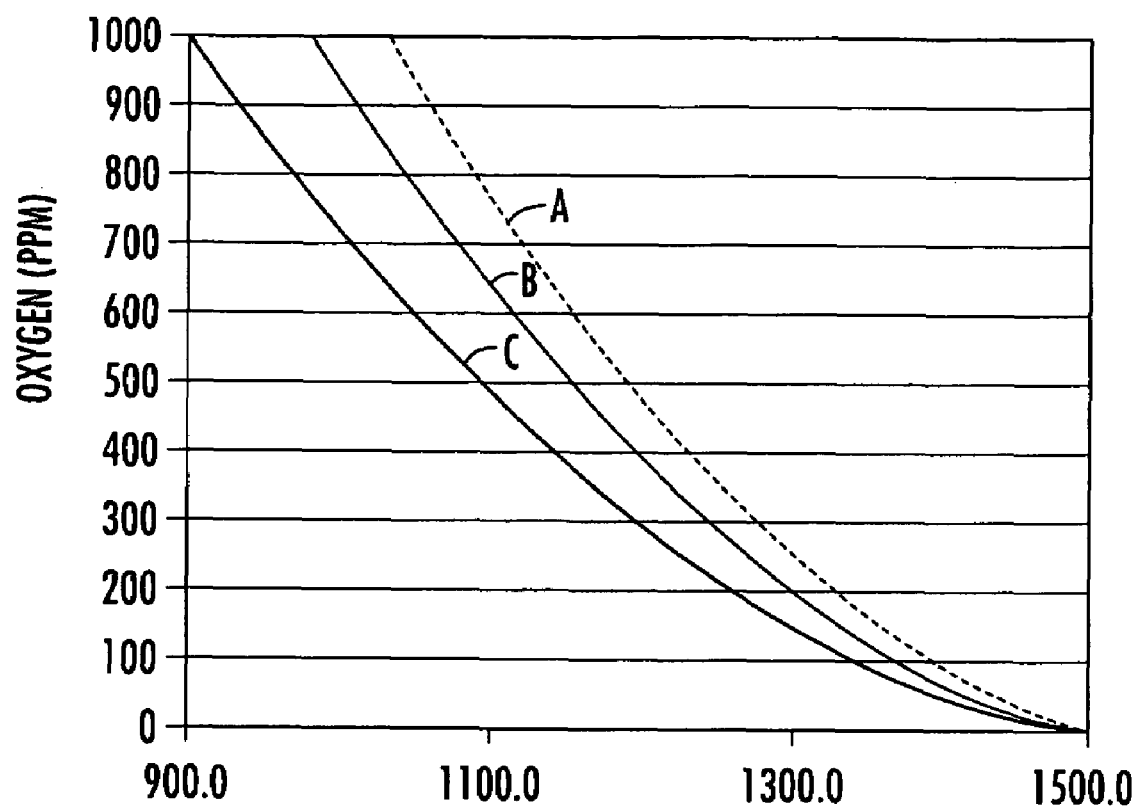
FIG. 3 is a graphical illustration in which oxygen concentration was measured at three different temperatures for a specific luminescent compound, which shows that as the oxygen concentration approaches zero, all three plots converge to a single point for all temperatures.

Applicants have discovered that the oxygen concentration can be determined over a wide temperature range by applying a mathematical function that describes the luminescent intensity of the luminescent compound as a function of oxygen concentration and temperature. The Applicants have recognized that as the oxygen concentration $[O_2]$ approaches zero, tau converges to a single unique tau value that is independent of temperature. In this regard, FIG. 3 is a graphical illustration in which oxygen concentration was measured at three different temperatures for a specific luminescent compound. FIG. 3 shows that as the oxygen concentration approaches zero, all three plots converge to a single point for all temperatures. Curves A, B, and C may be described by the following second-order polynomial equations:

$$\text{Curve } A: A = A_{Ta}(T)^2 + B_{Ta}(T) + C_{Ta} \quad (2)$$

$$\text{Curve } B: B = A_{Tb}(T)^2 + B_{Tb}(T) + C_{Tb} \quad (3)$$

$$\text{Curve } C: C = A_{Tc}(T)^2 + B_{Tc}(T) + C_{Tc} \quad (4)$$

wherein T is the temperature at which the data for each curve A through C was determined and $A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are coefficients that describe the behavior of respective curve as a function of temperature. The measured data may be used to solve for the 9 coefficients by performing a curve-fit operation. To provide the most accurate results, it may be desirable to use a curve fit program that provides $r^2$ values in excess of 0.90 and that may approach 1.0, such as SigmaPlot graphing software that is available from SYSTAT.

The 9 coefficients are specific to the luminescent compound for which they were determined and may be treated as constants in subsequent operational steps. As discussed in greater detail below, curves A, B, C may be determined for a wide variety of luminescent compounds, from which a set of 9-coefficients for each luminescent compound may be determined.

In one embodiment, curves A, B, and C may define a temperature range that encompasses the expected temperature of the container(s) to be examined. For example, if it is expected that the container(s) to be examined will have a temperature from about 10 to 15° C., it is advantageous to determine curves A and C at temperatures that are below and above the expected temperature range of the container, respectively. Curve B may be determined at some temperature between that of curves A and C. It should be recognized that the temperatures of the container(s) may be extended outside the temperature range at which curves A and C were determined and the present invention can still operate, although not necessarily with the same accuracy in the results.

Applicants have discovered that the following equation can be constructed for calculating the oxygen concentration:

$$[O_2] = A(\text{tau})^2 + B(\text{tau}) + C \quad (5)$$

From equations 2-5 the oxygen concentration may be determined by measuring the temperature of the luminescent compound and the intensity of the emission as a function of time. The intensity measurements may then be used to plot a decay curve, from which tau can be calculated. The oxygen concentration is then calculated by using the 9 coefficients and the measured temperature to solve for A, B, and C of equations 2-4, followed by using tau and the calculated A, B, and C values in equation 5.

Equations 2-5 can be combined to produce a single equation that is a function of both temperature and the measured tau:

$$[O_2] = (A_{Ta}(T)^2 + B_{Ta}(T) + C_{Ta})(\text{tau})^2 + (A_{Tb}(T)^2 + B_{Tb}(T) + C_{Tb})(\text{tau}) + (A_{Tc}(T)^2 + B_{Tc}(T) + C_{Tc}) \quad (6)$$

wherein T is the same as above and the 9-coefficients are the same as described above.

The value of tau can be determined from the intensity data utilizing a number of different methods. In one method, tau is determined by calculating the area under the decay curve. In this embodiment, tau is determined by integrating the area under the curve according to the following equation:

$$A = \int_0^\infty e^{-t/\tau} dt = \tau \qquad (7)$$

wherein: A is the area under the decay curve and t is time.

The calculated tau is then used to determine the oxygen concentration as described above.

Figure 4:
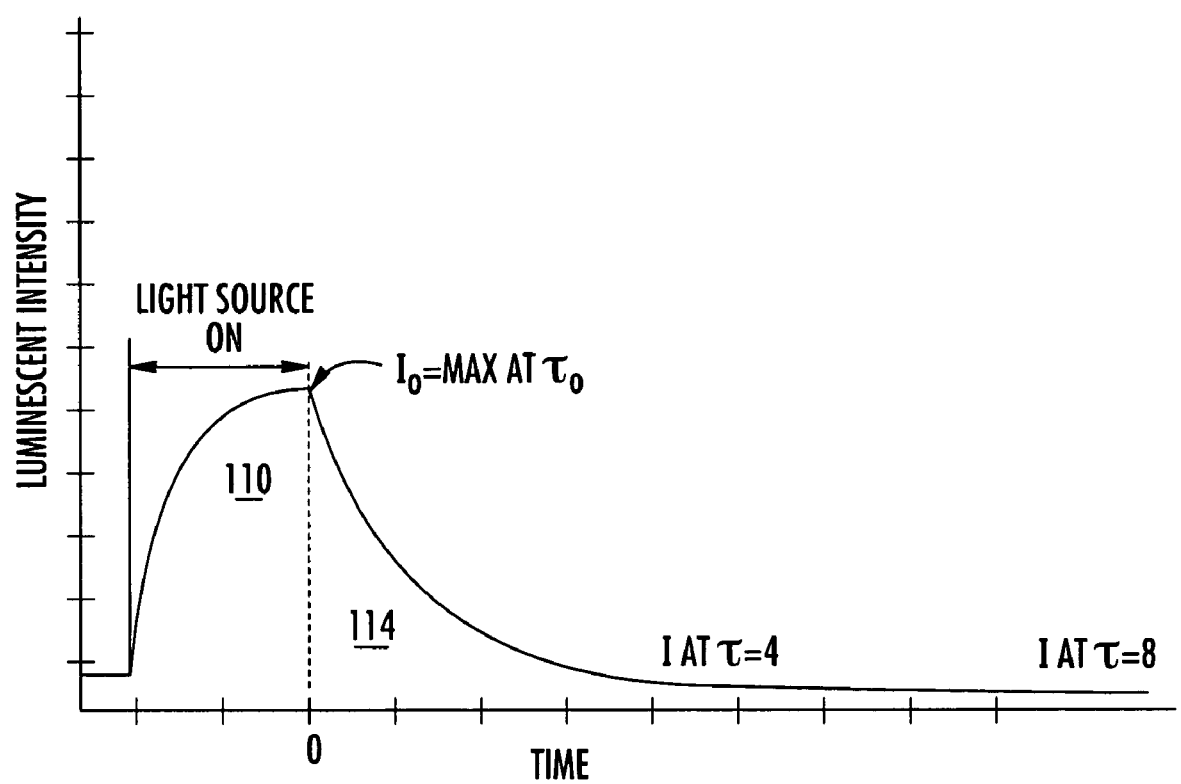
FIG. 4 is graphical illustration of an exponential decay curve that shows the time necessary to "pump" the luminescent compound, and the approximate positions of 4 and 8 tau.

In this embodiment, a luminescent compound may be excited by exposing it to an exciting light source. Typically, it takes a discrete amount of time for the luminescent compound to become "pumped" so that a maximum emission intensity $I_0$ is obtained. At this maximum emission a steady-state exists wherein the populations of the excited and ground states are in equilibrium. In this regard, FIG. 4 illustrates an exponential decay curve that depicts a luminescent compound being excited until a maximum intensity is reached. This time period is represented by reference number 110. Once a steady state has been obtained, the exciting light source is turned off and intensity measurements begin. This is time=0 or $I_o$=max and is represented by reference number 112. After the exciting light source has been turned off, the excited luminescent molecules transition to the ground state. At time=0, emission intensity is measured as a function of time. The resulting measurements may then be used to plot the decay curve, which is represented as reference number 114. In one embodiment, intensity measurements may be taken for a length of time that is equal to or greater than 4 tau.

The intensity measurements may be taken in discrete time segments. For example, an intensity measurement is taken from about every 1 μs to 30 μs. The rate at which intensity measurements are taken may depend in part, on the lifetime of the luminescent compound that is being excited. For example, every luminescent compound has a unique lifetime that is specific to that compound. Some luminescent compounds have an average excited lifetime on the order of 100 ms, while others have an excited lifetime that is less than 100 μs. For luminescent compounds having relatively short excited lifetimes it may be desirable to take each intensity measurement within a relatively short time duration of each other, such as every few microseconds or less. In some embodiments, taking an insufficient number of intensity measurements may introduce error into the calculation because the resulting data may not accurately reflect the exponential decay curve, which may result in an inaccurate determination of tau. The time segments may then be summed to produce an overall curve of intensity values.

The intensity measurements typically include a baseline signal that is not due to the emissions of the luminescent compound. This so called "noise" results from stray light, background noise, electronic noise, and the like. The noise typically includes small amounts of positive and negative noise that can partially cancel each other out. In one embodiment, the noise or baseline area may be measured and then subtracted from the summed intensity values so that the remaining intensity values are from the luminescent emission. The baseline area value may be determined before the excitation light source has been turned off or after the luminescent compounds have returned to the ground state, such as after at least 4 tau. This is discussed in greater detail below.

Figure 5A:
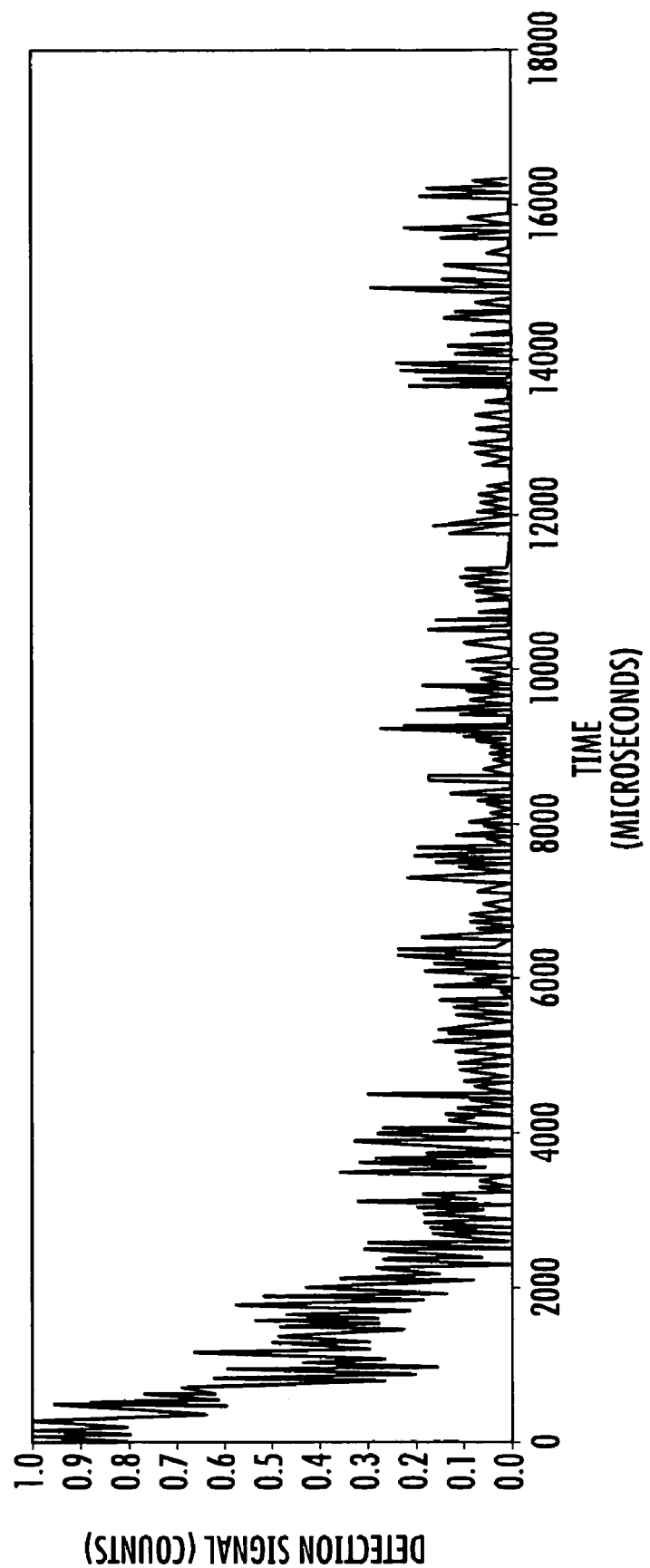
FIGS. 5A through 5C are graphical plots of a detection signal as a function of time and how signal averaging may be used to reduce the level of noise in the intensity signal.
Figure 5B:
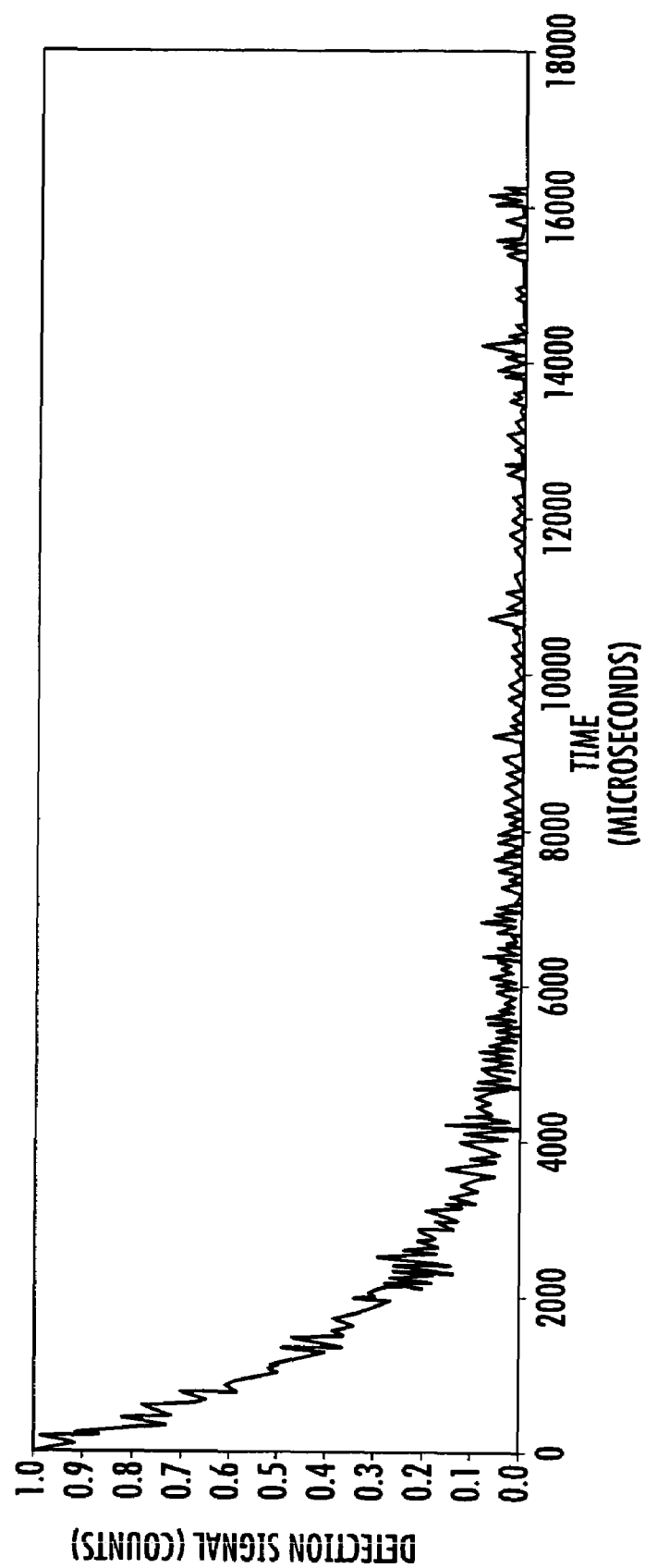
Figure 5C:
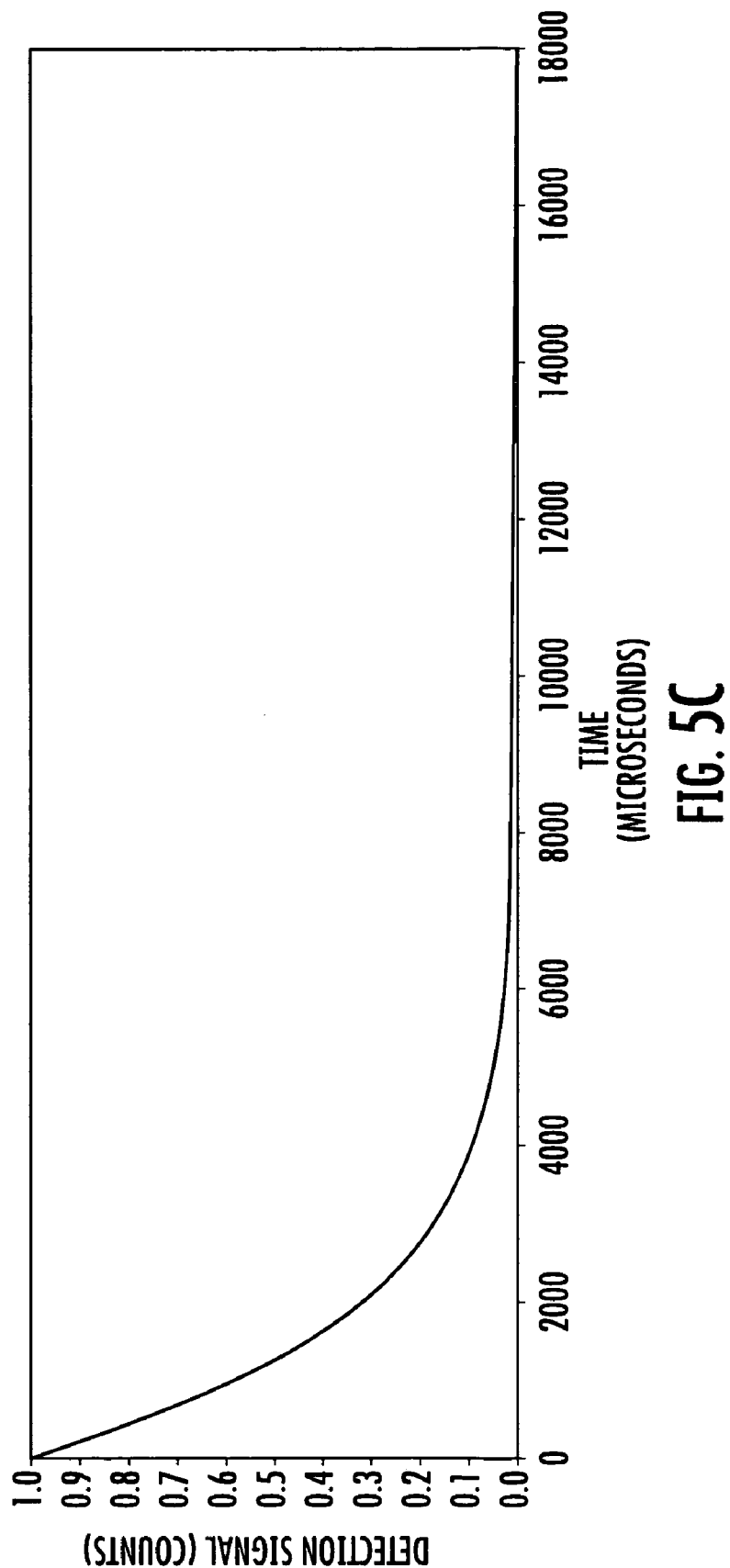

Signal averaging can be used to improve the quality of the data and further reduce the level of noise. In signal averaging, the luminescent and decay process is repeated n number of times. Since the excited lifetimes of luminescent compounds are relatively short, on the order of $10^{-4}$ to $10^2$ seconds for fluorescence transitions, a luminescent compound can be excited and permitted to decay multiple times in a short amount of time. In some embodiments, the luminescence and decay process is repeated from hundreds to thousands of times, and n is greater than 10, 100, 200, 300, 400, 500, 1000, 2000, or 2500. By averaging the signal n number of times, the signal-to-noise ratio may be improved and a more accurate determination of oxygen concentration is determined. In this regard, FIGS. 5A-5C illustrate some of the noise reducing advantages that may be obtained with signal averaging. FIG. 5A is a graphical plot in which n=1 and that illustrates the large amount of noise that may be present within a single plot. FIG. 5B is a graphical plot in which n=10. From FIG. 5B it can be seen that signal averaging may significantly eliminate much of the noise that may be present in the signal. FIG. 5C is a graphical plot in which n=1500. In FIG. 5C a substantial amount of the noise has been removed and the exponential decay curve has a clean appearance.

After baseline subtraction and normalization, tau is determined by calculating the area under the curve using equation (8) above. Utilizing integration or summing to calculate the area under the curve helps to provide a more accurate result because the integral process essentially nulls the random highs and lows that may be present in the measured signals. As a result, an average signal is produced that provides a more accurate measurement of the oxygen concentration. Other methods that may be used include derivative or differential processes, such as curve fitting. However, derivative or differential processes may not provide as accurate a result as integration because they tend to be more sensitive to noise.

Figure 6:
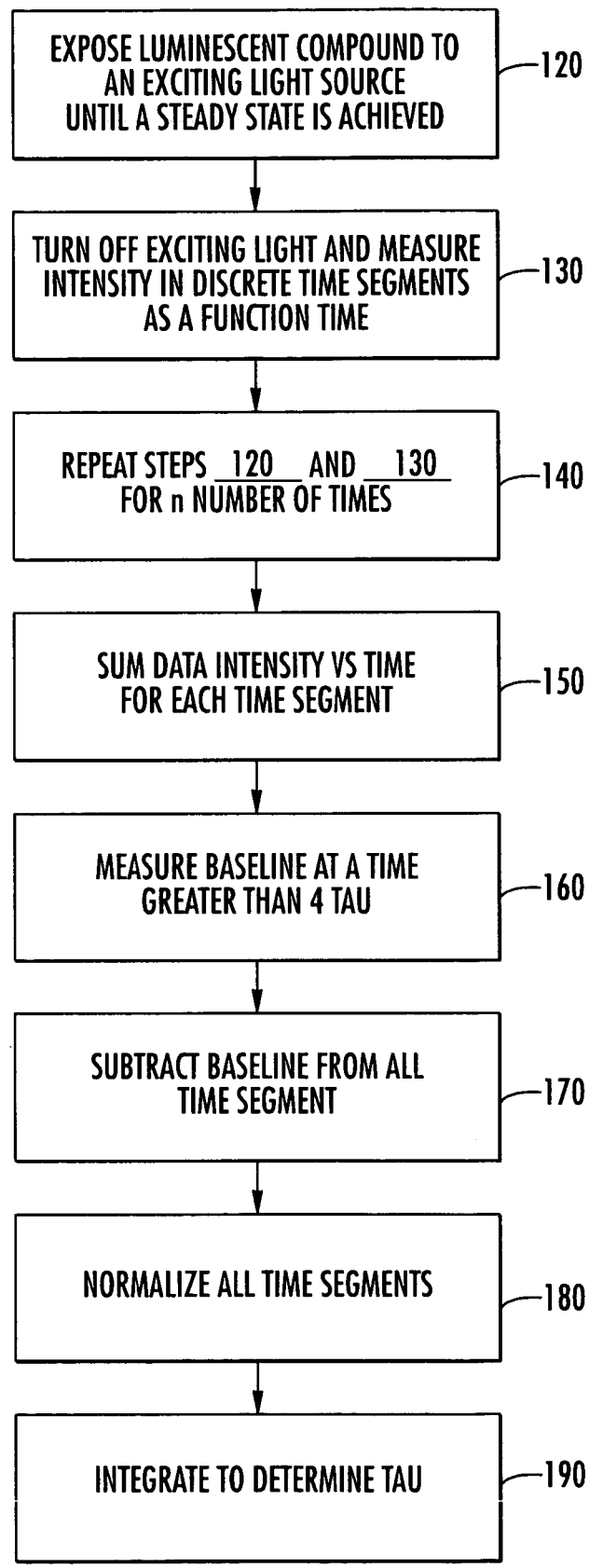
FIG. 6 is a block diagram depicting in step-wise a method of determining tau.

With reference to FIG. 6, a block diagram representing one alternative embodiment of calculating tau is illustrated. In step 120, a luminescent compound is excited by exposing it to an excitation light. The luminescent compound is exposed to the excitation light until a steady state is achieved. While in this steady state, the populations in the excited state and ground state are in equilibrium. At step 130 the source of the excitation light is turned off and the measurement of emission intensity is begun. The time point at which intensity measurements begin is referred to as t=0. In one embodiment, each intensity measurement is done as a time segment. Steps 120 and 130 are then repeated n number of times at step 140. After the process has been repeated n number of times, the intensities as a function of time for each time segment are summed at step 150. In step 160 the baseline is measured at a time greater than 4 tau. A plot of intensity as a function of time produces an exponential decay curve. In steps 170 and 180 the baseline is subtracted from all time segments that were summed in step 150 and then normalized. In step 190 the area under the curve is then calculated to determine tau. As discussed above, tau may then be used with the 9 coefficients and the measured temperature to determine the oxygen concentration.

To improve the accuracy of the calculation, it may be useful to determine the baseline at values greater than 4 tau. In this regard, FIG. 4 illustrates the intensity of the signal as the luminescent compound is excited to a steady state. Upon reaching the steady state, the exciting light source may be turned off so that emission intensity produces an exponential decay curve. In determining the baseline, inaccuracies in the calculation of the oxygen concentration may occur if the measurement of tau is prematurely stopped at some point that is less than 4 tau. Typically, the exponential decay curve is an asymptotic curve that continues to approach the true value of the baseline as the curve extends to infinity. If the measurements are prematurely cut-off and the baseline determined at this point two sources of error may occur. For instance, prematurely determining an end point for the intensity measurements may result in a baseline value that may be too high and which may include some signal that is a result of the emissions from the excited luminescent compound. If this baseline is subtracted from the intensity measurements it may result in a portion of the emission intensity being subtracted from the overall intensity data. Additionally, a second portion of the decay curve that includes emission intensities of the luminescent compound may not be included in the intensity data. To prevent this from occurring, it may be desirable to include intensity measurements and determine the baseline at a value greater than at least 4 tau. In some embodiments, the area of the exponential decay curve may include intensity measurements at values greater than 8 tau or 10 tau.

An additional problem may arise if the baseline signal is too low. In the integration process, only positive values are integrated and any negative noise values (i.e., below the x-axis) will not be included in the area calculation. To avoid this problem, the instrumentation of the apparatus is adjusted so that the baseline is greater than any noise having a negative value. This may be accomplished by manual adjustment or could be controlled as an automatic function of the apparatus.

Once tau has been determined, the oxygen concentration is calculated using equation (8) described above. In one embodiment, the method includes the use of equation (8) and the 9 coefficients that were previously determined. Typically, each luminescent compound has an emission lifetime that is specific to that compound. Similarly, the 9 coefficients are also specific to the luminescent compound for which they were determined. In one embodiment, the 9 coefficients for a specific luminescent compound may be predetermined and stored in a control unit or its associated memory. The 9 coefficients for the luminescent compound may be recalled to determine the oxygen concentration within a container having the luminescent compound for which the 9 coefficients were determined. In some embodiments, the control unit and/or an associated memory may include the 9 coefficients for a plurality of luminescent compounds.

Luminescent compounds that may be used in the practice of the invention include compounds whose molecules are able to be promoted to an excited state by absorbing a photon and then relax to the ground state by emitting a photon, and wherein such an emission is quenchable by oxygen. Suitable luminescent compounds may include compounds that undergo fluorescence and/or phosphorescence transitions that are capable of being quenched by oxygen. In one embodiment, the luminescent compound comprises a phosphorescent compound that is oxygen quenchable.

Each luminescent compound is typically excited at a specific wavelength that may be different than the wavelengths at which other luminescent compounds are excited. Additionally, the excited luminescent compound may emit light at a wavelength that may be specific to that luminescent compound. As discussed in greater detail below, the device for exciting the luminescent compound and measuring the resulting intensity data may be configured to output light that includes light having a wavelength that is specific to the luminescent compound that is being examined. In some embodiments, the device may be configured to recall information for a plurality of luminescent compounds so that the device may be used in conjunction with one or more luminescent compounds to determine the oxygen concentration within a sealed container. Also, the presence of carbon monoxide in the container does not interfere with the accuracy of the invention.

Suitable luminescent compounds may include porphyrins, meaning those compounds that contain the porphyrin ring structure (Monograph No. 7468, Tenth Edition of The Merck Index, Merck & Company, Inc., Rahway, N.J., 1983), chlorins, bacteriochlorins, and isobacteriochlorins. The porphyrin ring structure gives rise to intense optical absorption and emission in the wavelength range of interest. The wavelengths for absorption and emission can be shifted by various chemical modifications to the porphyrin ring structure. In addition, the emission lifetimes may be strongly dependent on any metal incorporated into the center of the ring. Suitable porphyrins that may be used include metal porphyrins such as tetra(pentafluorophenyl)porphyrin (TFPP), octaethylporphyrin (OEP), tetraphenylporphyrin (TPP), and tetrabenzporphyrin (TBP) compounds. Suitable metals may include second and third transition row metals with electron configurations $d_6$ or $d_8$, including Ru(II), Rh(III), Pd(II), Os(II), Ir(III), Pt(II), and Au(III). Some other metalloporphyrins that may also be suitable include, for example, Hf(IV) octaethylporphyrin. Pd(II) and Pt(II) complexes of tetra(pentafluorophenyl)porphyrin (TFPP), octaethylporphyrin (OEP), tetraphenylporphyrin (TPP), and tetrabenzporphyrin (TBP) may be particularly useful. The luminescent compound may comprise a metal porphyrin that undergoes a phosphorescent transition.

In some embodiments, the luminescent compound may be in the form of a label that has been adhered to an inner surface of window 32. The luminescent compound can be disposed in a carrier matrix, such as a polymer, and the polymer matrix is adherable to an interior surface of a sealed container (see briefly FIG. 11, reference number 30). In embodiments where the luminescent compound is disposed within a polymeric matrix, the polymer material should have sufficient permeability so that oxygen may diffuse through the polymeric material and collide with the luminescent compound. The luminescent compound can also or alternatively be present in a material, such as a varnish or resin, that is printed or otherwise applied onto an inner surface of window 32. As exemplary composition and label are discussed in greater detail in U.S. Pat. No. 6,689,438.

The range of sensitivity for any particular luminescent molecule used in the oxygen quenching-sensitive composition can be adjusted by choice of the carrier matrix and also the amount of any plasticizer that may be dissolved in the matrix. Polyvinyl chloride with variable amounts of plasticizer may provide suitable carrier matrices, as does polymethyl methacrylate without plasticizer. Other suitable oxygen-permeable matrices can be made of cellulose acetate or silicone-polybicarbonate copolymer.

Figure 7:
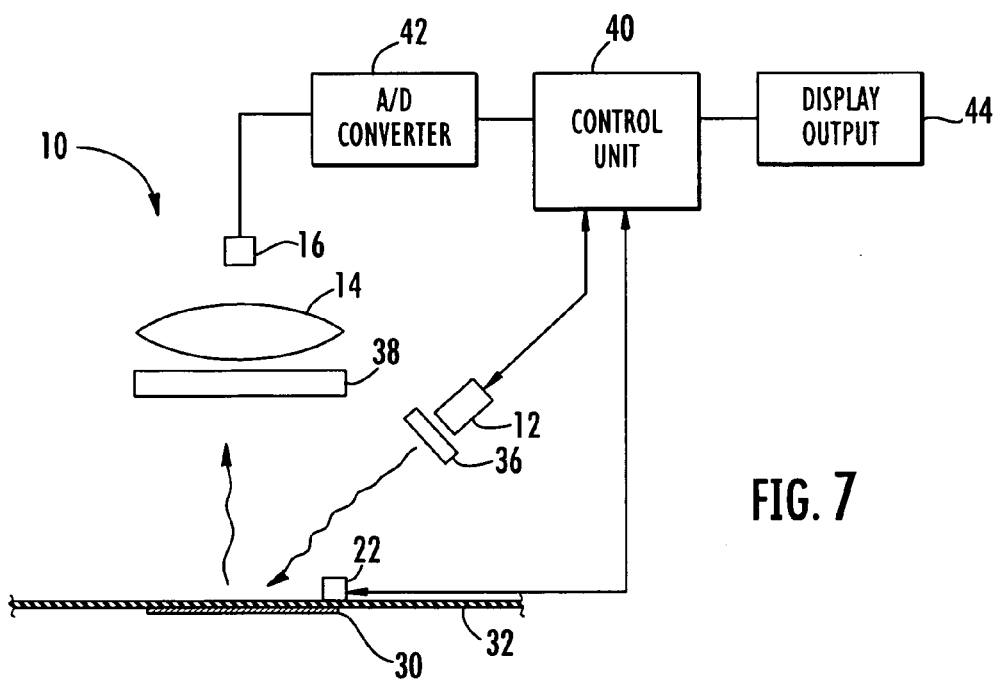
FIG. 7 is a schematic illustration of an apparatus for exciting a luminescent compound and measuring the resulting luminescent intensity wherein the apparatus includes a control unit.

With reference to FIG. 7, a schematic illustration of an apparatus for measuring oxygen concentration is illustrated and broadly designated as reference number 10. The apparatus 10 is depicted as being in an oxygen-measuring relationship with a luminescent compound 30. As discussed above, the apparatus 10 may include an excitation source 12, focusing optics 14, detector 16, and temperature sensor 22. The various components of the apparatus are operatively connected to a control unit 40, which can be an internal or external component of apparatus 10. In one embodiment, the control unit is configured to analyze the luminescent emission intensity and the temperature data to calculate the oxygen concentration within a container. As discussed in greater detail below, the control unit 40 can also be configured to control and adjust the operational parameters of the components of the apparatus, such as the excitation source 12. For example, the control unit may be configured to adjust the intensity of excitation light that is output by the excitation source. In some embodiments, the control unit may also include various executable program modules that are configured for calculating the oxygen concentration within a container, and for operatively controlling the various components and functions of the apparatus.

As illustrated, the apparatus may include an analog-to-digital converter 42 ("A/D converter"). The A/D converter permits conversion of the electronic signals from the detector 16 into digital values that are processed by the control unit. The A/D converter may comprise a 12 bit converter having an output as a number from 0 to 4095. In some embodiments, the control unit 40 is capable of adjusting the various components of the apparatus to ensure that the converted intensity data is within the number range of 0 to 4095.

The apparatus 10 may also include an output display 44 such as an LCD display. The output display visually displays the oxygen concentration of the container being examined. The output display may also be used to indicate one or more of: the measured concentration of oxygen within the container; the status of the apparatus, which may include whether the apparatus has successfully determined the oxygen concentration of the container; power status; menu options; operational mode; and the like. In some embodiments, the apparatus also includes an output device that is capable of producing an audible output that may be used in lieu of, or in combination with, a visual display. The apparatus may be configured to generate both a visual output and an audible output.

Figure 8:
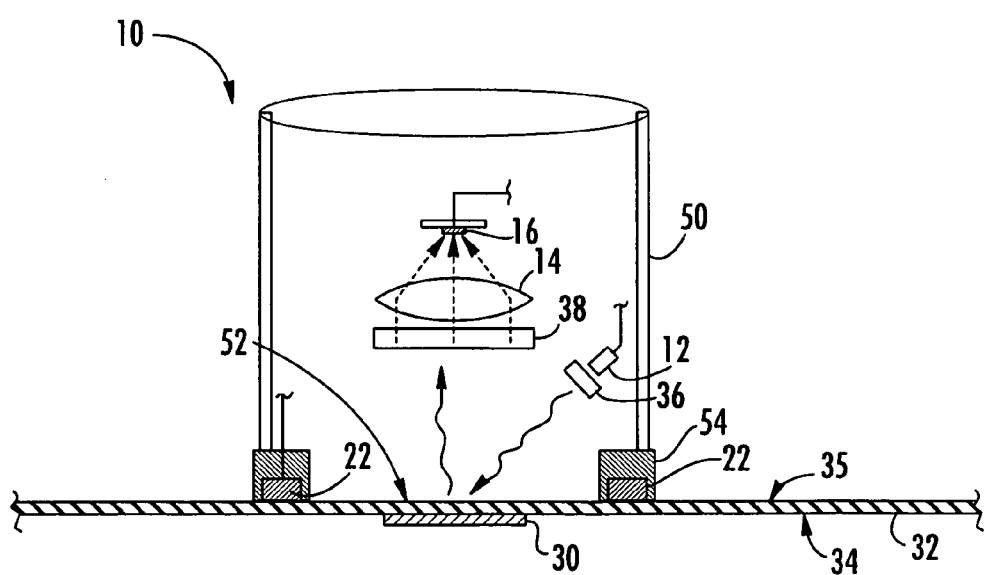
FIG. 8 is a cross-sectional side view of an apparatus for measuring oxygen concentration wherein the apparatus includes an insulating member that can thermally isolate the housing from the container.

With reference to FIG. 8, a cross-sectional view of apparatus 10 for measuring oxygen concentration within a container is illustrated. In one embodiment, the apparatus 10 comprises a handheld device having a housing 50 that is configured to be portable and easily supported by an operator. The housing 50 may comprise a material that is lightweight and strong, such as a thermoplastic material. As shown, the various components for exciting the luminescent compound and collecting the luminescent emissions are disposed within housing 50. The housing 50 may have a generally cylindrical shape, which cylindrical shape permits an operator to easily grip and manipulate the apparatus.

The housing 50 includes an opening 52 defining an aperture through which excitation light generated by the excitation source 12 exits the housing and luminescent light enters the housing. The size of the opening is configured so that a substantial portion of light emitted by the luminescent compound enters the apparatus and is collected via focusing optics 14. The use of a relatively large aperture and focusing optics increases the amount of light that the apparatus is able to collect and thereby improves the sensitivity of the apparatus. Additionally, the use of a relatively large aperture permits some leeway in the positioning of the apparatus with respect to the luminescent compound. As a result, an operator is able to quickly position the apparatus in an oxygen measuring relationship with luminescent compound without having to find an exact position for the apparatus. In one embodiment, the aperture has an f-stop of about 2. In some embodiments, the detector 16 may be slightly offset from the focal point of the focusing optics. As a result, the detector may provide a greater surface area upon which the light can impact.

Accurately measuring the temperature of the window 32, and hence, the interior space of the container helps to improve the accuracy of the oxygen concentration measurement. From equations (2)-(4) above, it can be seen that the calculated values of A, B, and C are a function of temperature, and therefore the calculation of the oxygen concentration is also a function of temperature. As a result, any error associated with determining the temperature may introduce significant error into the calculation of oxygen concentration. The Applicants have discovered that limiting heat from the surrounding environment and from the electronics of the apparatus helps improve the accuracy of the calculated oxygen concentration.

To help improve the accuracy of the temperature measurement the apparatus can include an insulating member 54 that is disposed between the housing 50 and an outer surface 35 of the window 32. The insulating member helps thermally isolate the window 32 from the housing 50. Further, one or more temperature sensors 22 may be disposed adjacent to the insulating member 54 so that the temperature sensors are also thermally isolated from the housing. The insulating member helps thermally isolate the temperature sensors from the surrounding environment. The insulating member comprises any suitable material that can be used to thermally isolate the temperature sensors. Suitable material includes thermoplastic or thermoset polymeric materials. The insulating member may comprise a black foam that helps prevent outside light from entering through the aperture.

The temperature sensor may be capable of accurately measuring the temperature of the luminescent compound being evaluated within about ±0.1° C. The temperature sensor 22 may comprise a resistance temperature detector (RTD) that may be positioned in direct contact with window 32. In embodiments where the temperature sensor comprises an RTD or similar sensor, an accurate temperature measurement may be obtained by positioning the temperature sensor in contact with window 32. In some embodiments, a wide variety of temperature sensors may be used including, for example, infrared, thermocouple, thermopile, RTD, and the like.

The excitation source 12 may be configured to emit light having a wavelength that is absorbable by the luminescent compound and sufficient to excite the luminescent compound to a higher energy state. The excitation source may comprise a solid state light source such as a light emitting diode (LED) and emit light having a peak wavelength between about 200 to 600 nm. In one embodiment, the excitation source comprises a UV light emitting diode having a peak wavelength between 300 and 450 nm, and in particular a UV LED having a wavelength of approximately 380 nm. In particular, the peak excitation wavelength of the excitation source may approximate the absorption wavelength of the luminescent compound. Other excitation sources may include flashlamps, tungsten halogen lamps, lasers, laser diodes, and the like. The device may also include two or more excitation sources 12.

As discussed in greater detail below, the apparatus 10 may be configured so that the intensity of the light emitted by the excitation source is selectively controlled so that the resulting intensity of the luminescent emission is likewise controllable. In some embodiments, the control unit is configured to adjust the output of the excitation source 12 so that the resulting electronic signal is converted into a digital number within a range of 0 to 4095. Luminescent emissions having too strong of a signal may result in saturation of the detector.

The detector 16 can comprise any detector that is capable of measuring light emitted by excited luminescent molecules as they transition from an excited state to the ground state. In one embodiment, the detector comprises a photodiode detector that is capable of converting light impacting the detector into an electronic signal. In some embodiments, the detector is able to measure the intensity of light comprising a range of wavelengths that is between about 600 to 1000 nm. Some luminescent compounds may have emission peaks in the range of about 650 to 780 nm. When exciting such luminescent compounds, solid state detection circuitry, such as photodiodes can be used. The detector may comprise a PIN photodiode detector. It should be recognized that other detectors may be used, such as a photomultipliers although not necessarily with results of the same accuracy.

In some embodiments, the apparatus includes focusing optics 14 that collect the emitted light and focus it onto the detector. The focusing optics may comprise one or more convex lenses and one or more prisms, such as a Fresnel lens, which are capable of focusing and intensifying the emitted light. Using a focusing lens to intensify the light permits the device to have improved sensitivity without an increase in background noise that may be associated with methods of electronically magnifying the signal, such as amplifiers.

In some embodiments, the apparatus includes one or more filters 36, 38 that filter out light of undesirable wavelengths and permit the transmission of light that is of interest. In some cases, the excitation source may emit light comprising a range of wavelengths, which may include a peak wavelength that approximates the absorption wavelength of the luminescent compound. This range of light may also include light having wavelengths that may not be absorbed by the luminescent compound and therefore do not excite the luminescent compound. In some cases, such light may be reflected back in the direction of the detector, which may result in the detector measuring the reflected light along with the light emitted by the excited luminescent compound. In other cases, stray light from the surrounding environment may also impact the detector. The light from the surrounding environment and the reflected light are collectively referred to as "background light." The measurement of this background light may result in an increase in the background noise that is measured. Although the additional noise may be subtracted from the luminescent intensity data, it may be problematic at relatively higher oxygen concentrations. For instance, at higher oxygen concentrations the intensity of luminescent light which is produced by excited luminescent molecules may be reduced due to oxygen quenching. At higher oxygen concentrations the intensity of luminescent light may be reduced to a greater extent. In some cases, a relatively large amount of background noise may dwarf the emission signal, which may increase the difficulty in differentiating the measured light that is due to the excited emissions and that which is the background or noise. This may result in decreasing the device's sensitivity at higher oxygen concentrations. To help reduce the background noise level, the apparatus may include filters 36, 38 that may filter out certain undesirable wavelengths of light. As a result, the filters may help reduce or limit that amount of background light that reaches the detector and may also help improve the sensitivity of the apparatus.

As discussed above, the apparatus may include one or more temperature sensors that are used to determine the temperature of window 32, and hence, the temperature of the interior space of the container. In some embodiments, the temperature sensor may be capable of accurately measuring the interior temperature of the container being evaluated within about ±0.1° C. The temperature sensor 22 may comprise a resistance temperature detector (RTD) that may be positioned in a temperature-monitoring relationship with the luminescent compound. In the context of the invention, a temperature-monitoring relationship refers to a position of the temperature sensor with respect to the container wherein the temperature sensor may be capable of measuring the interior temperature within about ±2° C. of its true temperature. In some embodiments, the temperature sensor may be capable of measuring the interior temperature within about ±1° C. of its true temperature. In embodiments where the temperature sensor comprises an RTD or similar sensor, a temperature monitoring relationship may be obtained by positioning the temperature sensor in contact with window 32.

In one embodiment, the control unit comprises a microprocessor or microcontroller configured to perform dedicated functions such as controlling the device and executing program modules that are capable of retrieving and analyzing the emission intensity data. The control unit may also include memory components such as RAM, EEPROM, and PROM, internal timers, and I/O port interfaces. The control unit may include an internal memory component (not shown) that may be an integral part of the control unit. In some embodiments, the control unit may include executable program modules embedded within the internal memory component of the control unit. In other embodiments, the control unit may be configured to recall one or more executable program modules from an associated memory component.

As discussed above, the control unit may be configured to analyze the emission luminescent intensity data to calculate tau. The control unit may include one or more algorithms, including equations (6) and (7) for calculating oxygen concentration and tau, respectively. The control unit may also include the above-described operational steps that may be used in the calculation of tau and the oxygen concentration. Such operational steps may include baseline determination, signal averaging, normalization, etc. In one embodiment, the control unit can also include the 9 previously determined coefficients that are used in equation (6) to calculate the oxygen concentration. The 9-coefficients are specific to the luminescent compound for which they were determined. The control unit may include a plurality of the 9-coefficients that are stored therein. In one embodiment, an operator may select an appropriate set of 9-coefficients that are specific for the luminescent compound being examined.

In one embodiment, the control unit is in communication with a memory component in which the one or more algorithms, operational steps, and plurality of 9-coefficients may be stored. The associated memory component can be internal or external to the control unit. The associated memory may include one or more stored executable program modules. The executable program modules may include the above described algorithms, operational steps, and the stored coefficients. The memory component may also include operational parameters that are specific to the luminescent compound being examined so that the apparatus may be used with a plurality of luminescent compounds having widely differing luminescent lifetimes, peak excitation wavelengths, luminescent intensities, and the like.

The apparatus may be configured to determine the oxygen concentration using a wide variety of different luminescent compounds. For instance, in one embodiment, an operator may input information relating to the specific luminescent compound into the apparatus via a user interface. From this, the operational parameters for exciting the luminescent compound and measuring the resulting luminescent intensity can be recalled. Such operational parameters may include, for example, the intensity of the excitation light and gain. Additional information that may be recalled includes any operational steps for calculating tau that are specific to the luminescent compound and the 9-coefficients. In some embodiments, an operator may select the appropriate luminescent compound from a plurality of luminescent compounds that may be presented to an operator via a visual display. In other embodiments, the apparatus may include a data entry device (e.g., bar code scanner or radio frequency identification (RFID) transceiver) that may be in communication with the control unit. In this embodiment, the container may include a code, such as a bar code, RFID tag, or other symbology that is disposed on the container. The code may include an identification code that can be used to recall the operational parameters for the luminescent compound. In some embodiments where the container includes an RFID tag, the RFID tag itself may be capable of communicating the operational parameters and other information specific to a particular luminescent compound to the control unit. An operator may use the data entry device to scan a representation of the identification code and input the code into the control unit.

In some embodiments, an operator can manually input the desired operational parameters into the apparatus. The control unit may then use the inputted parameters to excite the luminescent compound and measure the resulting luminescent emissions.

As discussed above, the control unit in some embodiments may be an external device that may be operatively connected to the apparatus 10. For example, in one embodiment, the control unit may be in the form of an external computer, such as a personal digital assistant (PDA), that may be external to apparatus 10. In this embodiment, the apparatus 10 for measuring the oxygen concentration is operatively connected to the control unit via wire or wireless connectivity means. In some embodiments, the external control unit includes a microprocessor and an associated memory component. The external control unit may also include a visual display comprising one or more of the features described above.

Figure 9A:
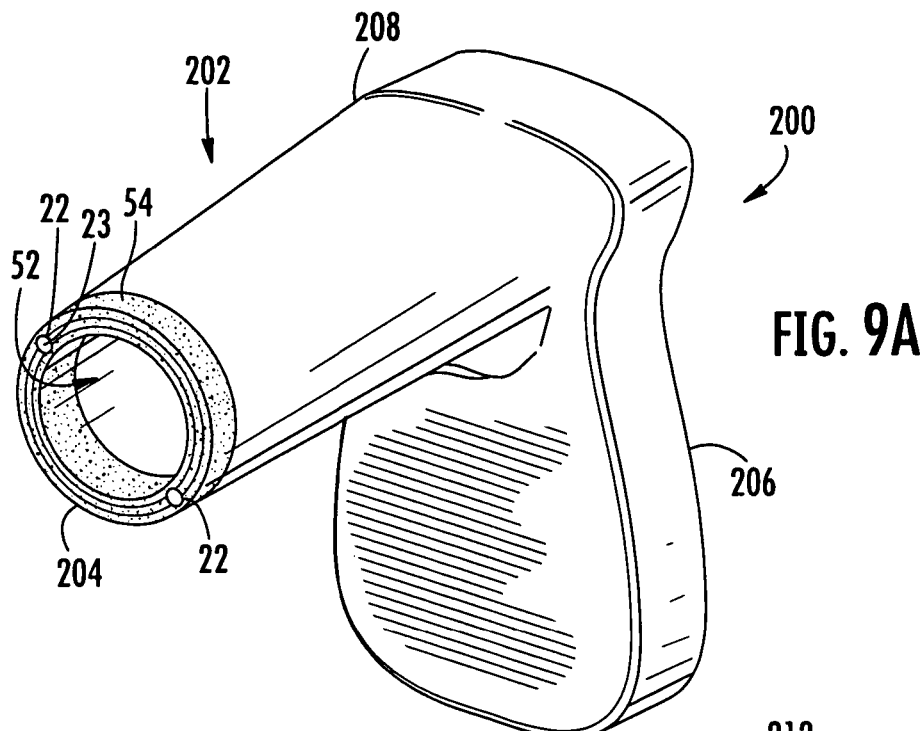
FIGS. 9A and 9B are perspective views of an apparatus for measuring oxygen concentration wherein the apparatus has a "gun-like' shape.
Figure 9B:
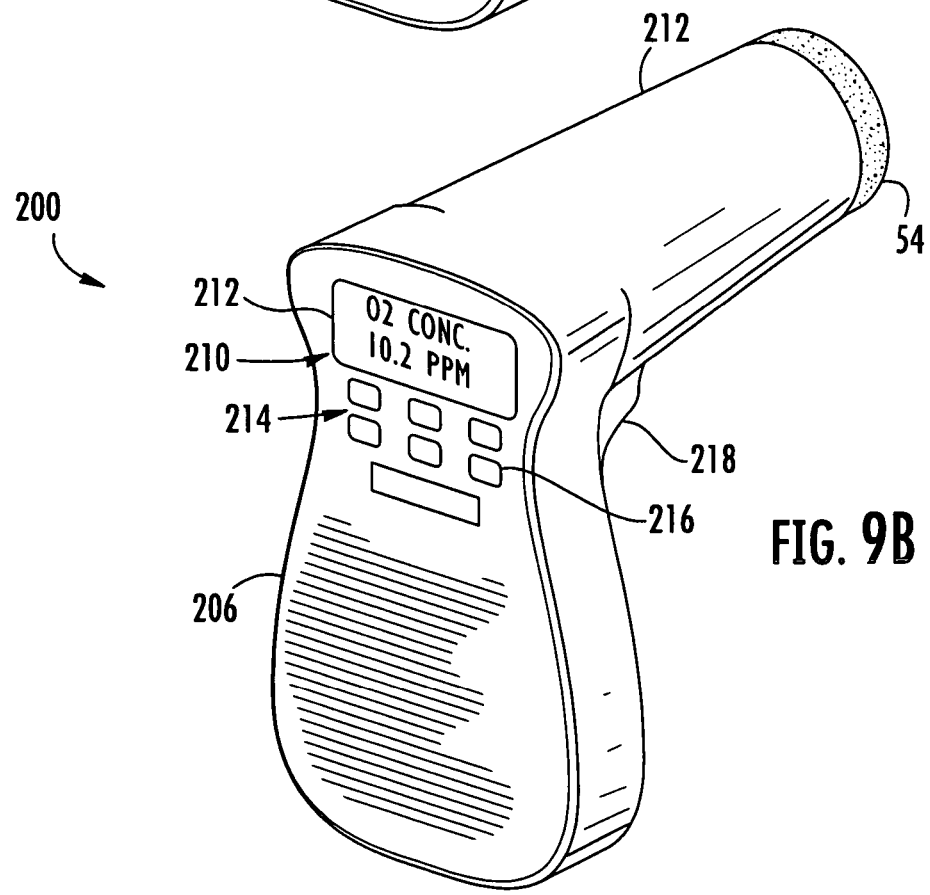

With reference to FIGS. 9A and 9B, an exemplary handheld apparatus for measuring oxygen concentration is illustrated and broadly designated by reference number 200. In some embodiments, the handheld apparatus may be capable of performing real-time analysis of the oxygen concentration within a container. The handheld apparatus may also be configured to visually display the calculated oxygen concentration.

As shown, the handheld apparatus may comprise a generally tubular housing member 202 having an opening 52 disposed at a distal end 204 thereof, the opening defining an aperture through which excitation light generated by the excitation source may exit the housing member and through which luminescent light emitted by an excited luminescent compound may enter into the housing member. The housing member may have a generally cylindrical shape. In some embodiments, the handheld apparatus 200 may include a handle member 206 that is attached to a proximal end 208 of the housing member 202.

In one embodiment, the components of the handheld apparatus, such as the excitation source, focusing optics and detector may be disposed in the housing member. The housing member may also include various filters and electronic components described above. The various components may be positioned within the housing member so that excitation light generated by the excitation source is able to exit through the opening and be absorbed by a luminescent compound, and so that luminescent light emitted by the excited compound may enter into the housing member so that it is detectable by the detector. In one embodiment, the components of the handheld apparatus may be arranged in a similar manner to that which is illustrated in FIG. 8.

The housing member 202 may also include an insulating member 54 that is disposed at the distal end 204 of the housing member. One or more temperature sensors may be disposed adjacent to the insulating member. In some embodiments, the one or more temperatures sensors 22 may be substantially encapsulated within the insulating member except for an outer surface 23 that comes into contact with an outer surface (see briefly FIG. 8, reference number 35) of the container being examined. As discussed above, the insulating member enables the container and the one or more temperature sensors to be thermally isolated from the housing member and the electronic components disposed therein. In some embodiments, the insulating member may have an annular-like shape.

The handheld apparatus 200 may include a handle member 206 that is attached to a proximal end 208 of the housing member. The handle member may provide a means whereby an operator may easily grip and manipulate the handheld apparatus 200. In one embodiment, the handle member may permit an operator to position and hold the opening of the housing member in contact with a container so that the handheld apparatus is in an oxygen measuring relationship with a luminescent compound disposed in an interior of the container. In one embodiment, the handheld apparatus may have a "gun-like" shape. In another embodiment, the handle member may have a pistol-like grip having a shape that is configured to fit a hand.

In one embodiment, the handle apparatus includes a user interface panel 210, which may include a visual display 212 and a user interface 214. The user interface may include one or more buttons or switches 216 that can be configured to allow an operator to input instructions and select among various menu options. In some embodiments, the buttons 216 comprise a touch sensitive keypad that allows an operator to operate the apparatus by applying pressure to a button within the keypad. The visual display may be adapted to display the status of the apparatus, such as operational mode, measured oxygen concentration within the container, menu options, and the like.

The handheld apparatus may also include one or more dedicated buttons or switches that may be used to initiate exciting the luminescent compound and measuring the resulting luminescent light. In some embodiments, this dedicated button or switch may be in the form of a trigger 218 that may be activated by an operator applying a squeezing action to the trigger. The trigger may permit the activation of the apparatus once an operator has positioned the handheld apparatus in a temperature measuring relationship with a container.

The user interface may be in communication with a control unit (not visible). In some embodiments the user interface may permit an operator to input operational parameters for the handheld apparatus into the control unit. In other embodiments, the user interface panel may permit an operator to scroll through a menu of various luminescent compounds from which the operator can select the luminescent compound that is disposed in the container. Thereafter, the control unit may be configured to apply a set of operational parameters that are associated with the selected luminescent compound. In other embodiments, an operator may manually select various operational parameters from a menu of such parameters.

The handheld apparatus may also include one or more data entry devices that may be integrated into the housing member or that may comprise a separate device that is operatively connected to the control unit. Data entry devices are discussed in greater detail above.

Figure 10:
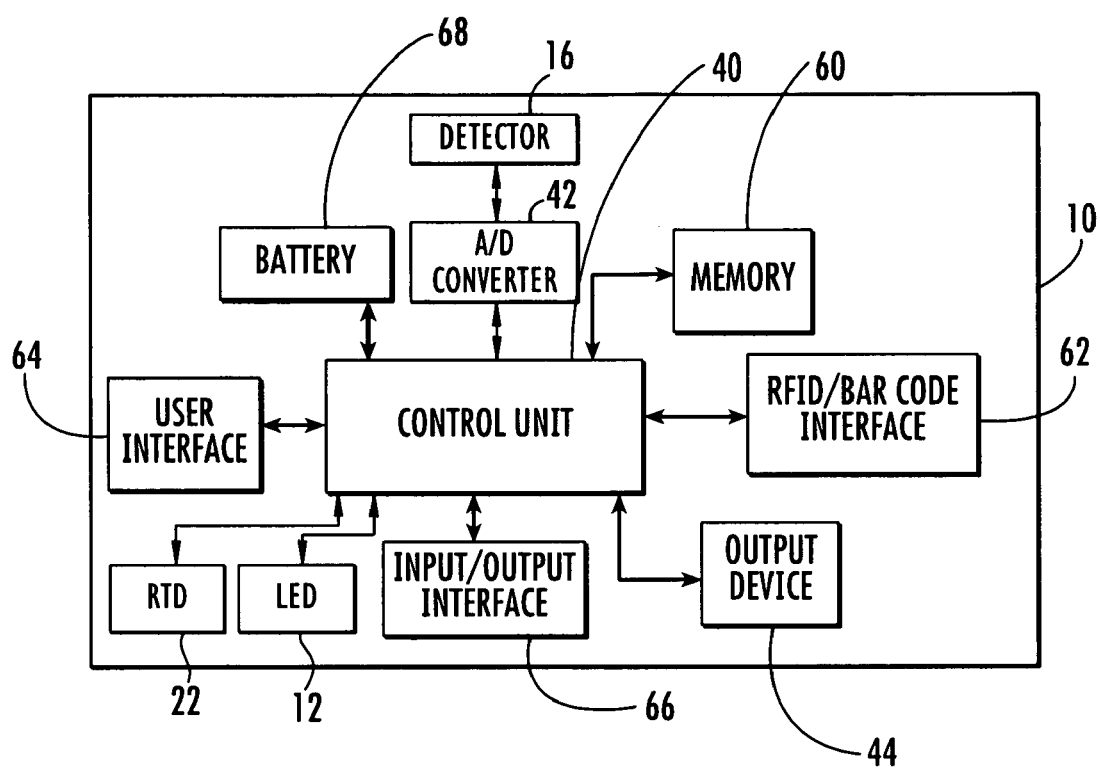
FIG. 10 is a schematic illustration of the various components that the oxygen measuring apparatus may include.

With reference to FIG. 10, the internal components of an exemplary apparatus 10 for measuring oxygen concentration in a container are illustrated. The apparatus may include a control unit 40, an excitation source 12, a detector 16, one or more temperature sensors 22, and an A/D converter 42. In some embodiments, the device may also include a memory component 60, a first interface 62 that may be adapted for reading or inputting a representation of an identification code, such as machine readable code or radio frequency identification (RFID) tag, a user interface 64, a second interface 66 adapted for communicating with an external computer, such as an input/output interface, a power supply such as a battery 68, and an output device 44, such as a visual display, that is capable of generating a sensory output. As shown in FIG. 10, the various components may be operatively connected to one another.

In some embodiments, the first interface 62 comprises a data input interface that is capable of inputting an identification code into the control unit. In some embodiments, the container in which the luminescent compound is disposed includes a representation of an identification code that may be attached to the container. The representation of the identification code may permit data representing the identification code to be inputted or read into the control unit. The control unit may then use the identification code to recall stored information for the luminescent compound. The stored information may include the optimal instrumentation for performing the excitation and measurement functions, the 9 coefficients for one or more luminescent compounds, one or more algorithms and operational steps for calculating the oxygen concentration, Tau, and the like. In one embodiment, the first interface includes an RFID transceiver that is adapted to allow the apparatus to retrieve data from an RFID tag. In some embodiments, the RFID communication interface may also be adapted to retrieve or write information from and to an RFID tag. The RFID transceiver may be capable of performing read only or read-write communications depending on the application. In other embodiments, the first interface 62 may be operatively connected to, or comprise, a data entry interface that is capable of inputting an identification code into the control unit. In some embodiments, a representation of the identification code may be encoded onto the container in the form of, for example, symbolic, alpha, or numeric information embodied in or on a machine- or human-readable identification code, such as a tag or label (e.g., bar coded tag or label), hole pattern, or radio frequency identification ("RFID") transceiver attached or printed onto the container. In one alternative embodiment, the representation of the identification code may comprise a bar code that is printed onto the container or that is in the form of a label attached to the container.

The second interface 66 may be adapted to send and retrieve data from an external computer or database. In some embodiments, the second interface may include input/output (I/O) interface. The I/O interface may comprise wired or wireless connectivity means such as I2C, ACCESS.bus, RS-232, universal serial bus (USB), IEE-488(GPIB), LAN/Internet protocols such as TCP/IP, wireless means such as infrared (IR) communication, 802.11x, and Bluetooth, etc. In some embodiments, the I/O interface may comprise a combination of wired and wireless connectivity means.

The user interface 64 may include a touch sensitive keypad having one or more buttons that are adapted to allow an operator to input operational instructions into the control unit or apparatus, or scroll through available menu options.

The associated memory component 60 may comprise a memory that may be configured to store operational parameters for one or more luminescent compounds, one or more algorithms for calculating oxygen concentration, the 9 coefficients for a plurality of luminescent compounds, and the like. In one embodiment, the associated memory component may be configured to store emission intensity data and oxygen concentration calculations. In one embodiment, the associated memory component may comprise flash memory. Flash memory refers generally to a type of nonvolatile memory that can be erased and reprogrammed in units of memory called blocks. The capacity of the memory component can be varied depending upon the desired amount of data that can be stored before downloading the data into an external computer or similar device. In some embodiments the capacity of the associated memory component may comprise, for example, 64K, 128K, 256K, or 512K memory blocks.

In one embodiment, the associated memory component may be configured to store information, such as measured oxygen concentration, temperature data, and luminescent emission data for a plurality of containers. At a desired time, the stored information can then be transmitted to an external computer. In some embodiments, the reader is adapted to store data from multiple containers before the data is transferred to an external computer.

Figure 11:
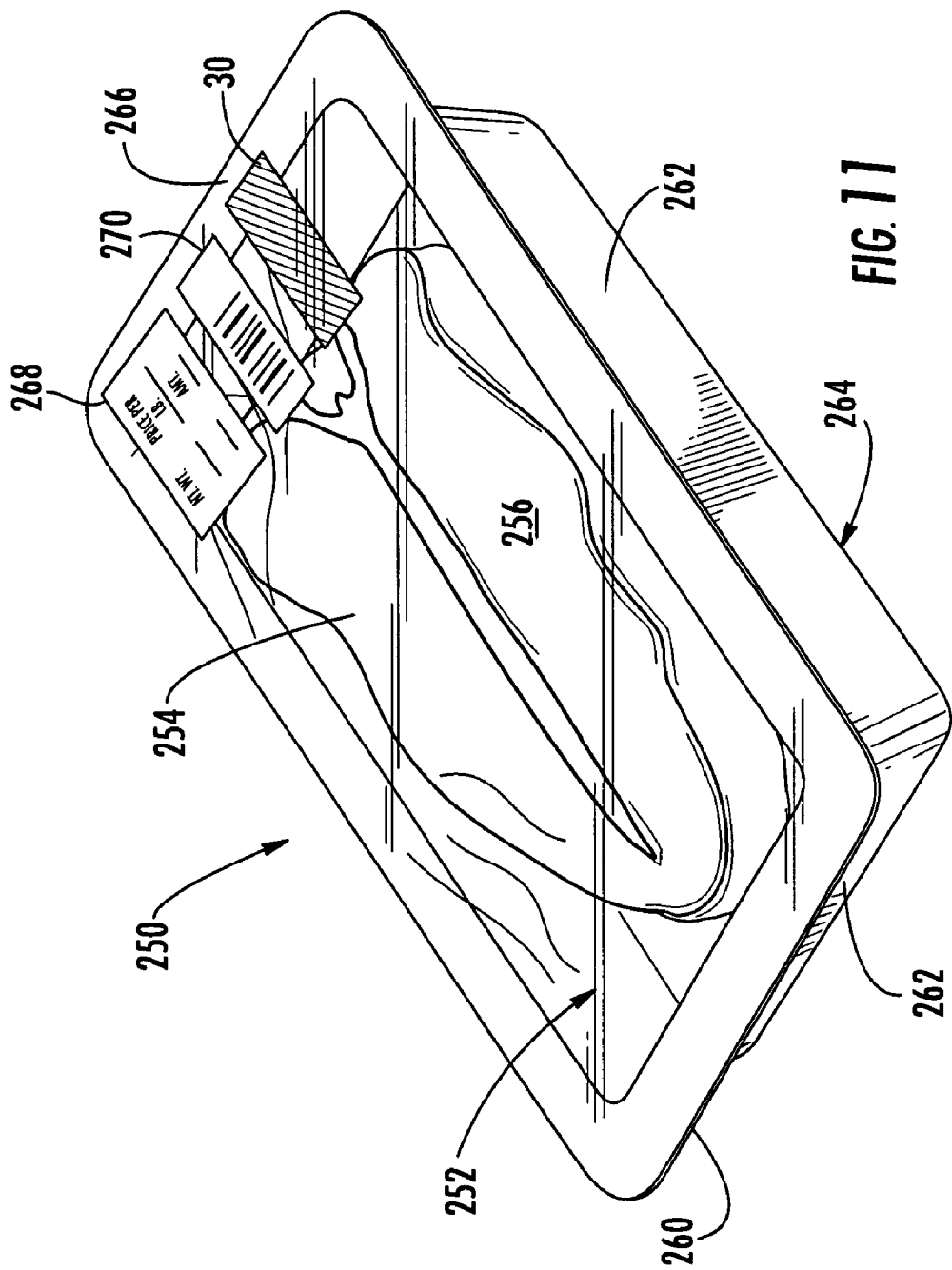
FIG. 11 is a perspective view of a sealed package having a luminescent compound attached to an inner surface of the lidstock.

In one embodiment, the invention may be particularly useful for measuring the oxygen concentration in a sealed container, such as a sealed package. In this regard, FIG. 11 illustrates a sealed package 250 having a luminescent compound disposed in an interior space of the package. In one embodiment, the package 250 may include a package having an interior space or cavity 252 in which an oxygen sensitive product, such as a food product 256 may be disposed, and a luminescent compound 30 disposed in an oxygen quenching relationship with the interior of the package 250. In one embodiment, a lidstock, such a film may enclose the product 256 and the luminescent compound within the package. Lidstock 254 may comprise an oxygen barrier film that may substantially prevent ingress or egress of oxygen in and out of the package. In one embodiment, the lidstock is transparent to the excitation light that is used to excite the luminescent compound and luminescent light that is emitted by the luminescent compound.

The term "package" as used herein shall be defined as any device for holding an oxygen sensitive product, such as raw meat, including a container, carton, casing parcel, holder, tray, flat, bag, pouch, film, case-ready packaging, envelope, bottle etc. In one embodiment, the invention may be used to measure the oxygen concentration of a sealed container having a food product, such as meat product, disposed therein.

In one embodiment, the package 250 may include product support member 260 having a cavity 252 or interior space formed therein and a product 256 disposed within the cavity. Support member 260 may be in the form of a tray having side walls 262 and a base 264 which define the cavity 252, and further may include a peripheral flange 266 extending outwardly from the cavity. Lidstock 254 forms a lid on the package 250 and encloses the product 256 within cavity 252 by being heat-welded or otherwise bonded to flange 266. In some embodiments, the lidstock 254 may be attached to the support member using other means including adhesive bonding, ultrasonic bonding, etc. In one embodiment, the package 250 may include a label 268 that may include product information, such as pricing, description, expiration date, etc. Label 268 may be placed on the package at the point of packaging or by the retailer at the point-of-sale.

Support member 260 can have any desired configuration or shape, e.g., rectangular, round, oval, etc. Similarly, flange 266 may have any desired shape or design, including a simple, substantially flat design which presents a single sealing surface as shown, or a more elaborate design which presents two or more sealing surfaces, such as the flange configurations disclosed in U.S. Pat. Nos. 5,348,752 and 5,439,132, the disclosures of which are hereby incorporated herein by reference.

In one embodiment, the package 250 may comprise a modified atmosphere package having a low or high oxygen concentration. To maintain the desired atmosphere within the package, the lidstock and the support member may have barrier properties that substantially prevent the ingress or egress of oxygen in and out of the package. Representative materials that may be used as the lidstock are discussed in commonly owned U.S. patent application Ser. No. 11/375, 711 entitled NON-INVASIVE METHOD OF DETERMINING OXYGEN CONCENTRATION IN A SEALED PACKAGE, filed Mar. 13, 2006, the contents of which are hereby incorporated by reference.

In FIG. 11 the luminescent compound 30 is depicted as being disposed on an inner surface of the lidstock 254. To measure the oxygen concentration within the package 250, an operator would position the oxygen sensing apparatus (see briefly FIGS. 8 and 9A) in contact with the lidstock so that the apparatus is in oxygen-measuring relationship with the luminescent compound. While in the oxygen-measuring relationship, the opening of the apparatus may substantially cover the luminescent compound. In embodiments having a temperature sensor, the insulating member may be placed in contact with the lidstock so that the one or more temperature sensors are able to maintain contact with the lidstock. In some embodiments, the insulating member may also maintain thermal and light isolation between the surrounding atmosphere and the portion of the lidstock that is covered by the apparatus.

After the apparatus is positioned correctly with respect to the luminescent compound, an operator may activate the excitation source and begin directing excitation light against the luminescent compound. Once the luminescent compound has reached a steady-state, the excitation source is shut-off and the detector measures the intensity of the luminescent light as a function of time. As discussed above, the control unit uses the resulting intensity data and temperature data to calculate the concentration of oxygen in the package.

In some embodiments, the package 250 may also include a representation of an identification code 270, such as a bar code, that is attached or printed on to the package. As discussed above, the identification code may be used by an operator to recall information relating to the specific luminescent compound including the optimal operational parameters for obtaining luminescent intensity data for the luminescent compound, the 9 coefficients to be used in conjunction with equation (8) above to calculate oxygen concentration, and the like.

In addition to determining oxygen concentration in a container, the invention may also be used to determine the rate at which oxygen is transmitted across a layer of film or other structure. In one particularly useful embodiment, the oxygen transmission rate through a film may be determined across a wide temperature range.

EXAMPLES

The following examples are provided for illustrative purposes only and should not be construed as limiting the invention.

In the following examples a palladium porphyrin was placed into a temperature controlled chamber through which a stream of gas having a known oxygen concentration was introduced into the chamber. The chamber included a window onto which an apparatus in accordance with the invention was placed in an oxygen and temperature monitoring relationship with the porphyrin. The porphyrin was exposed to a light at a peak wavelength around 380 nanometers. The luminescence of the excited porphyrin was measured over a period of time ranging between 0 and 8,000 μs to produce an exponential decay. For each measurement the excitation and luminescence cycle of the porphyrin was repeated 1000 times. The baseline signal was determined at a time that is about 5,000 tau. The resulting cycles were averaged from which tau was calculated. Temperature was determined with a RTD that was placed in a temperature monitoring relationship with the porphyrin.

The results in Table 1 demonstrate that the apparatus and method can be used to quickly determine the oxygen concentration within a sealed chamber. It is noted, that for oxygen concentrations below 200 ppm, the calculated oxygen concentration has greater error than at concentrations above 400 ppm. The Applicants believe that increases in inaccuracy at concentrations below 200 ppm result from prematurely cutting-off the baseline signal for the exponential decay curve. As discussed above, this may result in a portion of the intensity signal not being included in the exponential decay curve. This source of error is magnified at lower oxygen concentrations because there is reduced quenching at low oxygen concentrations and the exponential decay curve is more parametric. Thus, Tables 1 through 3 demonstrate the effect of prematurely cutting-off the baseline when calculating tau.

TABLE 1

| $O^2$ concentration (ppm) | Measured Temperature (° C.) | Tau (μs) | Inventive Calculated $O_2$ concentration (ppm) |
|---|---|---|---|
| 0 | 2.44 | 1488.8 | 9.8 |
| 0 | 2.44 | 1487.2 | 8.6 |
| 100 | 3.31 | 1411.0 | 64.8 |
| 100 | 3.31 | 1411.0 | 64.8 |
| 200 | 2.25 | 1333.7 | 180.0 |
| 200 | 2.25 | 1335.1 | 177.6 |
| 400 | 2.44 | 1223.8 | 406.8 |
| 400 | 2.44 | 1222.6 | 409.7 |
| 600 | 2.69 | 1156.5 | 581.5 |
| 600 | 2.69 | 1155.1 | 585.5 |
| 800 | 2.75 | 1086.2 | 795.9 |
| 800 | 2.81 | 1085.2 | 798.3 |
| 900 | 2.56 | 1055.4 | 903.4 |
| 900 | 2.56 | 1053.9 | 908.7 |
| 1000 | 2.69 | 1035.3 | 972.5 |
| 1000 | 2.69 | 1031.6 | 985.9 |

In Tables 2 and 3 the oxygen concentration was determined over a range of oxygen concentrations at 10° and 20° C., respectively. As in Table 1, it can be seen that the apparatus and method of the invention can be used to quickly determine the oxygen concentration within a sealed chamber, such as a package.

Tables 2 and 3 also demonstrate the effects that temperature has on the accuracy of the calculated oxygen concentration. The results in Table 1, were used to calculate the Stern-Volmer constant. The Stern-Volmer constant from Table 1 was then used in combination with the tau values in Tables 2 and 3 to calculate the oxygen concentration using the Stern-Volmer equation. It can clearly seen in Tables 2 and 3 that the Stern-Volmer equation does not accurately calculate the oxygen concentration at non-isothermal conditions.

In Table 2, the temperature within the chamber was held at about 10° C.

TABLE 2

| O² concentration (ppm) | Measured Temperature (° C.) | Tau (μs) | Inventive Calculated O₂ concentration (ppm) | Stern-Volmer Calculated O₂ concentration (ppm) |
|---|---|---|---|---|
| 0 | 10 | 1463.2 | 9.6 | 0 |
| 0 | 10 | 1463.2 | 9.6 | 0 |
| 100 | 10 | 1370.7 | 99.7 | 153.4 |
| 100 | 10 | 1370.7 | 99.7 | 153.4 |
| 200 | 10 | 1307.7 | 188.8 | 270.3 |
| 200 | 10 | 1307.7 | 188.8 | 270.3 |
| 400 | 10 | 1192.8 | 408.7 | 515.2 |
| 400 | 10 | 1192.8 | 408.7 | 515.2 |
| 600 | 10 | 1112.5 | 606.7 | 716.4 |
| 600 | 10 | 1112.5 | 606.7 | 716.4 |
| 800 | 10 | 1041.2 | 812.9 | 921.1 |
| 800 | 10 | 1041.2 | 812.9 | 921.1 |
| 900 | 10 | 1008.3 | 917.7 | 1025.4 |
| 900 | 10 | 1008.3 | 917.7 | 1025.4 |
| 1000 | 10 | 985.3 | 994.7 | 1102.3 |
| 1000 | 10 | 985.3 | 994.7 | 1102.3 |

In Table 3, the temperature within the chamber was held at about 20° C.

TABLE 3

| O² concentration (ppm) | Measured Temperature (° C.) | Tau (μs) | Inventive Calculated O₂ concentration (ppm) | Stern-Volmer Calculated O₂ concentration (ppm) |
|---|---|---|---|---|
| 0 | 20 | 1448.5 | 12.8 | 0 |
| 0 | 20 | 1448.5 | 12.8 | 0 |
| 100 | 20 | 1353.6 | 74.5 | 159.3 |
| 100 | 20 | 1353.6 | 74.5 | 159.3 |
| 200 | 20 | 1256.0 | 187.2 | 348.3 |
| 200 | 20 | 1256.0 | 187.2 | 348.3 |
| 400 | 20 | 1125.0 | 416.9 | 653.5 |
| 400 | 20 | 1125.0 | 416.9 | 653.5 |
| 600 | 20 | 1040.9 | 611.8 | 890.0 |
| 600 | 20 | 1040.9 | 611.8 | 890.0 |
| 800 | 20 | 965.4 | 818.3 | 1137.3 |
| 800 | 20 | 965.4 | 818.3 | 1137.3 |
| 900 | 20 | 933.3 | 915.2 | 1254.6 |
| 900 | 20 | 933.3 | 915.2 | 1254.6 |
| 1000 | 20 | 909.3 | 991.1 | 1347.7 |
| 1000 | 20 | 909.3 | 991.1 | 1347.7 |

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of measuring oxygen concentration in a container comprising:
providing a container having a luminescent compound disposed in an interior space of the container, the luminescent compound having a luminescent emission that is sensitive to quenching by oxygen;
irradiating the luminescent compound with light having a wavelength that is absorbed by the luminescent compound so that the luminescent compound is promoted into an excited state;
terminating the irradiation of the luminescent compound when the luminescent compound achieves a steady state between excitation and luminescence;
measuring luminescent intensity over a period of time to produce an exponential decay curve;
calculating the exponential coefficient of the curve to determine tau;
measuring a temperature that is indicative of the temperature of the luminescent compound during the time that the luminescent intensity is measured; and
calculating the oxygen concentration within the container using the following equation:

$$[O_2]=(A_{Ta}(T)^2+B_{Ta}(T)+C_{Ta})(\text{tau})^2+(A_{Tb}(T)^2+B_{Tb}(T)+C_{Tb})(\text{tau})+(A_{Tc}(T)^2+B_{Tc}(T)+C_{Tc})$$

wherein:
T is the measured temperature;
tau is the exponential coefficient of the decay curve; and
$A_{Ta}$, $B_{Ta}$, $C_{Ta}$, $A_{Tb}$, $B_{Tb}$, $C_{Tb}$, $A_{Tc}$, $B_{Tc}$, and $C_{Tc}$ are previously determined coefficients for the luminescent compound that describe the luminescent intensity of the luminescent compound as a function of oxygen concentration and temperature.

2. A method according to claim 1, wherein the step of calculating tau further includes
determining a baseline area for the exponential decay curve;
subtracting the baseline area from the area under the curve, and
normalizing the curve.

3. A method according to claim 1, wherein step of calculating the area of the exponential decay curve further includes integrating the area under the exponential decay curve.

4. A method according to claim 2, wherein the step of determining a baseline area comprises determining a baseline area at a point on the curve having a value of at least 4 tau or greater.

5. A method according to claim 2, wherein the step of determining a baseline area comprises determining a baseline area at a point on the curve having a value of at least 8 tau or greater.

6. A method according to claim 1, wherein the luminescent compound comprises a metal porphyrin.

7. A method according to claim 6, wherein the metal comprises palladium or platinum.

8. A method according to claim 1, wherein the step of measuring the temperature of the container includes the step of contacting an outer surface of the container with a resistance temperature detector.

9. A method according to claim 8, further comprising the step of thermally isolating the resistance temperature detector.

10. A method according to claim 1, wherein the steps of irradiating the luminescent compound, terminating the irradiation of the luminescent compound, and measuring luminescent intensity are repeated n number of times and wherein n is from about 10 to 2500.

11. A method according to claim 1, wherein the step of measuring luminescent intensity over a period of time further comprises:
taking an intensity measurement every 1 to 100 microseconds to create a plurality of discrete time segments;
repeating the steps of irradiating the luminescent compound, terminating the irradiation of the luminescent compound, and measuring luminescent intensity n number of times, wherein n is from about 10 to 2500 to create n number of discrete time segments;

summing the n number of discrete time segments.

12. A method according to claim 11, further comprising the steps of
   determining a baseline area for the exponential decay curve at a value of 8 tau or greater;
   subtracting the baseline area from all summed time segments;
   normalizing the summed time segments; and
   integrating the summed time segments to determine tau.

13. A method according to claim 1, further comprising the step of recalling the coefficients from a storage device.

14. A method according to claim 13, further comprising selecting the luminescent compound from a plurality of luminescent compounds, wherein the luminescent compound is associated with coefficients in the storage device.

15. A method according to claim 1, further comprising the step of positioning an apparatus having an excitation source, a detector, a temperature sensor, and a control unit in an oxygen measuring relationship with the container.

16. A method according to claim 1, wherein in the container comprise a sealed package having a modified atmosphere.

17. A method according to claim 1, wherein the step of measuring a temperature further comprises measuring the temperature of the container.

* * * * *

UNITED STATES PATENT AND TRADEMARK OFFICE
CERTIFICATE OF CORRECTION

| | | |
|---|---|---|
| PATENT NO. | : 7,569,395 B2 | Page 1 of 1 |
| APPLICATION NO. | : 11/375557 | |
| DATED | : August 4, 2009 | |
| INVENTOR(S) | : Havens et al. | |

It is certified that error appears in the above-identified patent and that said Letters Patent is hereby corrected as shown below:

Column 13,

Line 3, after "If the" insert --intensity--.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,569,395 B2
APPLICATION NO. : 11/375557
DATED : August 4, 2009
INVENTOR(S) : Havens et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 814 days.

Signed and Sealed this

Seventh Day of September, 2010

David J. Kappos
*Director of the United States Patent and Trademark Office*